United States Patent [19] [11] Patent Number: 6,090,373
Oshima et al. [45] Date of Patent: Jul. 18, 2000

[54] ULTRAVIOLET-SCREENING COMPOSITE PARTICULATE AND PROCESS FOR THE PRODUCTION THEREOF

[75] Inventors: Kentaro Oshima; Shunji Kozaki; Yoshinobu Imaizumi; Toshio Miyake; Keiichi Tsuto, all of Wakayama, Japan

[73] Assignee: Kao Corporation, Tokyo, Japan

[21] Appl. No.: 09/125,463

[22] PCT Filed: Feb. 17, 1997

[86] PCT No.: PCT/JP97/00420

§ 371 Date: Aug. 19, 1998

§ 102(e) Date: Aug. 19, 1998

[87] PCT Pub. No.: WO97/30934

PCT Pub. Date: Aug. 28, 1997

[30] Foreign Application Priority Data

Feb. 21, 1996 [JP] Japan ................................. 8-060016

[51] Int. Cl.[7] .............................. A61K 7/42; A61K 7/00; A61K 9/14; C09B 14/00; C09C 1/36
[52] U.S. Cl. ........................ 424/59; 106/425; 106/436; 106/442; 424/401; 424/489; 424/490
[58] Field of Search ..................... 424/401, 489, 424/490, 59; 106/425, 436, 442

[56] References Cited

U.S. PATENT DOCUMENTS 4,927,464  5/1990  Cowie ..................................... 106/436

FOREIGN PATENT DOCUMENTS

95/09895  4/1995  WIPO .

OTHER PUBLICATIONS

Japan Abstract: Ultraviolet–intercepting composite micro–particle, its production and cosmetic, JPA08012961, Jan. 16, 1996.

Japan Abstract: Spherical or randomly shaped Ti oxide of ave. particle size 30–70 nm is covered with hydrate comprising 1–4 wt. % (SiO2 conversion) of silicic acid hydrate and 6–12 wt. % (AL2O3 conversion) of alumina hydrate, JPA3115211, May 16, 1991.

*Primary Examiner*—Shelley A. Dodson
*Assistant Examiner*—Marina Lamm
*Attorney, Agent, or Firm*—Birch, Stewart, Kolasch & Birch, LLP

[57] ABSTRACT

Ultraviolet shielding composite fine particles having transparency in a visible light region, comprising matrix particles comprising an aggregate of primary particles having an average particle size of from 0.001 to 0.3 µm, the aggregate being formed while the primary particles retain their shapes; and daughter particles having an average particle size of from 0.001 to 0.1 µm, the daughter particles being dispersed in and supported by the matrix particles, wherein the daughter particles have a smaller band gap energy than the particles constituting the matrix particles and are capable of absorbing ultraviolet light, and wherein the surfaces of the composite fine particles are coated with one or more silicones selected from the group consisting of modified silicones, reactive silicones, and silicone-modified copolymers, and wherein the ultraviolet shielding composite fine particles have substantially no catalytic activities. By forming composite fine particles comprising the ultrafine particles having the ultraviolet shielding ability, the composite fine particles of the present invention have substantially no catalytic activities, high transparency in the visible light region, and high shielding ability in the ultraviolet light region.

20 Claims, 6 Drawing Sheets

ULTRAVIOLET-SCREENING COMPOSITE PARTICULATE AND PROCESS FOR THE PRODUCTION THEREOF

This application is the national phase under 35 U.S.C. §371 of prior PCT International Application No. PCT/JP97/00420 which has an International filing date of Feb. 17, 1997 which designated the United States of America, the entire contents of which are hereby incorporated by reference.

TECHNICAL FIELD

The present invention relates to ultraviolet shielding composite fine particles having substantially no catalytic activities, having high transparency in the visible light region, and a high shielding ability in the ultraviolet light region, and a method for producing the same.

BACKGROUND ART

Of the sunlight reaching the earth (including infrared light, visible light, and ultraviolet light), 5 to 6% is ultraviolet light. The ultraviolet light has short wavelengths, which are thus high-energy electromagnetic waves. Therefore, the ultraviolet light is known to decompose many kinds of materials and to cause quite some damages to a living body.

Therefore, ultraviolet shielding agents are used for protecting skin from inflammation or skin cancer due to the ultraviolet light by formulating them in the cosmetics, or they are mixed with paints to prevent a pigment from fading due to decomposition by ultraviolet light. In these cases, an unnatural skin whitening of the cosmetics and a color change of paints can be prevented by increasing the transparency in the visible light region. Therefore, the ultraviolet light is desirably blocked while the transparency in the visible light region is maintained.

The ultraviolet shielding agent comprising organic compounds used as effective ingredients prevents the transmission of the ultraviolet light on account of the specific absorption of ultraviolet light by the organic compounds. For example, an ultraviolet absorbing composition comprising substituted N,N'-bis-aromatic formamidines is known (Japanese Patent Examined Publication No. 61-09993). However, the organic ultraviolet shielding agents have the problem that although the absorbed ultraviolet light is at the same time likely to act to decompose, with the result of an undesirable lowering of the shielding ability over time. Regarding their application to cosmetics, the kinds and amounts of the ultraviolet shielding agents formulated are restricted owing to effects caused on human bodies, and thus it is difficult to achieve a good shielding performance within a controlled range. Furthermore, when they are used in high proportions, stickiness increases, resulting in an unpleasant feeling.

On the other hand, the ultraviolet shielding agent comprising an inorganic compound contains inorganic fine particles and prevents the transmission of ultraviolet light by the absorbing ability and the scattering ability of the composition. The inorganic ultraviolet shielding agent is superior to the organic ultraviolet shielding agent because the composition containing the inorganic ultraviolet shielding agent is not decomposed by the ultraviolet light with the passage of time and has little effects on the human bodies.

However, since the inorganic ultraviolet shielding agents are present in the form of particles, it is more difficult with inorganic ultraviolet shielding agents when compared with organic ultraviolet shielding agents to block the ultraviolet light while maintaining high transparency in the visible light region.

In order to exhibit an effective light shielding ability in the ultraviolet light region while maintaining high transparency in the visible light region (light wavelengths of from 400 to 800 nm), the composition has to be microgranulated to give ultrafine particles to be highly dispersed so as to increase the ultraviolet shielding ability (absorbing ability, scattering ability). However, in the case of using such ultrafine particles, problems may arise in the dispersion stability due to the aggregation of the ultrafine particles, and in the catalytic activities of the ultrafine particles.

In order to improve dispersibility, the ultrafine particle surfaces may be coated with other materials. For example, skin cosmetics comprising an oily cosmetic base material and a hydrophobic titanium oxide powder are known (Japanese Patent Examined Publication No. 59-15885). However, a suitable solvent has to be selected depending upon the properties of the coating layer formed on the surfaces. Also, since the particles are still ultrafine, the aggregation can only be lowered to a limited extent even if the surface treatment is conducted. In publications other than those mentioned above, there have been known cosmetics containing a powder obtainable by coating titanium oxide with a particular amount of mixed hydrates comprising silicate hydrates and alumina hydrates, wherein the titanium oxide is nearly spherical or irregularly shaped and having an average particle size of from 30 to 70 nm, and further by coating the surfaces with a silicone oil (Japanese Patent Laid-Open No. 2-247109). However, since in this publication the above powder is obtained by drying and pulverization of the product obtained after coating with the mixed hydrates comprising silicate hydrates and alumina hydrates or after coating the surfaces of the powder with the silicone oil, it is extremely difficult to pulverize the titanium oxide ultrafine particles to the size of the primary particles, namely the titanium oxide ultrafine particles are aggregated and have a large particle size, so that the transparency and the ultraviolet shielding ability of the above obtained powder are lowered. Such technological problems arise in maintaining the dispersibility of the ultrafine particles stable. Therefore, it is increasingly significant to find a way to achieve a high dispersibility of the ultrafine particles and maintain it at that level.

Also, for the purposes of solving the problem of a difficult handling of the metal oxide ultrafine particle powder and of easily providing cosmetics comprising uniformly dispersed ultrafine particles, starting materials for cosmetics comprising metal oxide ultrafine particles having a particle size of not more than 0.1 µm, a dispersion medium, and a dispersant, wherein the content of the ultrafine particles is not less than 10% by weight, have been known (Japanese Patent Laid-Open No. 6-239728). However, although the aggregation of the ultrafine particles and the deterioration of the dispersant, the dispersion medium, and cosmetics base materials caused by the catalytic activities of the metal oxide ultrafine particles are the problems to be solved, they have not been considered in this publication. Moreover, the content of the metal oxide ultrafine particles in the starting materials for cosmetics is limited to not less than 10% by weight by considering the amounts formulated in the cosmetics. However, as long as the metal oxide ultrafine particles are uniformly and stably dispersed, the function of the metal oxide ultrafine particles is high, and the content of the metal oxide ultrafine particles in the starting materials for cosmetics needs not be limited to an amount of 10% by weight or more for all kinds of cosmetics.

Therefore, in order not to lower the ultraviolet scattering ability by the aggregation of the inorganic ultrafine particles, composites of the inorganic ultrafine particles are often formed with other relatively large carrier particles. For example, a thin flaky material dispersed with metal compound fine particles is known (Japanese Patent Laid-Open No. 63-126818). However, this publication never discloses a specific construction of the fine particles for improving both the shielding ability of the ultraviolet light and the transparency of the visible light.

On the other hand, composite fine particles comprising ultrafine particles dispersed in and supported by the solid material are proposed. Conventional ultraviolet shielding composite fine particles include, for example, a composite powder in which a fine particle powder, such as $TiO_2$l is uniformly dispersed in plate particles of metal oxides, such as $SiO_2$ (Japanese Patent Laid-Open No. 1-143821); and composite particles in which a zirconium oxide powder or an aluminum oxide powder is carried on a surface of the matrix particles comprising such materials as nylon resins, silicone resins, and silicon oxide, wherein a titanium oxide powder or a zinc oxide powder is dispersed in an inner portion of the matrix particles (Japanese Patent Laid-Open No. 2-49717).

However, in order to use the above composite particles as ultraviolet shielding agents, the composite particles have to be usually dispersed in a medium in the actual environment. In this case, since the metal oxides, such as titanium oxide, contained in those composite particles have catalytic activities, the deterioration of the medium is likely to take place. Also, when the difference between the refractive index of the composite particles and the refractive index of the medium is large, light scattering takes place at an interface of the composite particles and the medium, thereby making both the transparency in the visible light region and the shielding ability in the ultraviolet light region poor. Although these problems need to be solved, they have not been considered in the above publications.

Therefore, in order to suppress the catalytic activities of the ultrafine particles, methods for coating a surface of the ultrafine particles with various materials have been used. For example, cosmetics comprising fine particle powder of titanium hydroxide which is obtained by hydrolysis of a titanium alkoxide is known, wherein a basic compound and a hydrocarbon compound having a boiling point of from 100 to 200° C. and/or a silicone having a particular molecular structure are added during the production (Japanese Patent Laid-Open No. 5-70331). However, in order to produce titanium hydroxide fine particle powder, the production process must undergo drying and pulverization processes, which results in a large particle size of the obtained titanium hydroxide fine particles. Thus, it is difficult for the particles to be highly exhibit scattering properties of ultraviolet light B (light wavelengths of from 280 to 320 nm), while maintaining high transparency in the visible light region. Also, the above publication has neither considered nor disclosed any method for producing ultrafine particles for the titanium hydroxide particles or methods for dispersing the ultrafine titanium hydroxide particles in cosmetics, in order to satisfy both high transparency in the visible light region and high shielding ability to the ultraviolet light. Moreover, the ultraviolet shielding material disclosed in this publication is considered to be effective, by titanium hydroxide or titanium oxide, in absorbing the ultraviolet light B (light wavelengths of from 280 to 320 nm), the ultraviolet light B only penetrating the epidermis and a relatively upper layer of the dermis and causing sunburn or skin cancers. However, they are not at all effective in absorbing the ultraviolet light A (light wavelengths of from 320 to 400 nm), especially the light having light wavelengths of from 350 to 400 nm, which are wavelengths close to those of the visible light, the ultraviolet light A reaching skin layers beyond the dermis and producing suntan or fibrous denaturalization in the dermis. In other words, the ultraviolet absorbents disclosed in this publication mainly exhibit absorption of the ultraviolet light B by titanium hydroxide or titanium oxide, but the exhibition of their ultraviolet absorption effects are limited to a light wavelength of up to about 300 nm for an anatase-type titanium oxide and to a light wavelength of up to about 320 nm for a rutile-type titanium oxide.

Of the ultraviolet light reaching the earth, the energy proportion of the ultraviolet light A is about 15 times that of the ultraviolet light B. Therefore, in view of the above energy proportion of the ultraviolet lights A and B, it is important to shield not only the ultraviolet light B but also the ultraviolet light A, rather than shielding the ultraviolet light B. Moreover, it is becoming increasingly important to shield both the ultraviolet light B and the ultraviolet light A, while maintaining a high transparency in the visible light region. In particular, in the case where the ultraviolet light A is shielded, it is important to shield light wavelengths of the ultraviolet light of from 350 to 400 nm, which are closer to light wavelengths of the visible light.

As mentioned above, in order to exhibit an effective shielding ability in the ultraviolet light region while maintaining and high transparency in the visible light region, the ultraviolet shielding materials are made ultrafine to be present in a highly dispersed state. In order to further improve the transparency in the visible light region, it is important to keep the difference between the refractive indices of the ultraviolet shielding materials and those of surrounding media small. In the titania-containing composite powders disclosed in Japanese Patent Laid-Open Nos. 1-143821 and 6-116119, the refractive index of the composite powder is determined by the compositional ratios of the components, and, therefore, it is inevitably limited to match the refractive index of the composite powder to the dispersion medium having a given refractive index value. Therefore, great problems have been encountered in controlling the refractive index of the composite powder so as to match it with the refractive index of the dispersion medium used. An effective solution for solving these problems has been in great demand.

Further, in metal compound-containing porous silica bead, the production method thereof, and the powder deodorant produced (Japanese Patent Laid-Open No. 4-65312), fine particles of metal compounds having a primary particle size of from 0.001 to 0.3 $\mu$m are contained in the particles of porous silica beads in an amount of from 0.1 to 30% by weight, and the porous silica bead contain substantially no voids of not less than 0.3 $\mu$m. In this case, when the fine particles of the metal compounds contained therein are suitably selected so as to have a refractive index close to the refractive index of silica (the refractive index being in the range of from 1.4 to 2.0), silica particles with further improved transparency can be obtained. However, only defined are the ranges for the refractive index of the metal compound fine particles contained in the inner portion of the composite particle, and the refractive index of the overall composite particles is not defined.

As explained above, in order to solve the problems inherent in the ultraviolet shielding agents comprising the ultrafine particles, several attempts have been made to utilize composites mainly comprising metal oxides. However, many of the compounds exhibiting good ultraviolet absorption properties, such as $TiO_2$ and ZnO, have relatively high refractive indices, so that the composite fine particles comprising composites of these ultrafine particles have refractive indices notably higher than aqueous solutions, conventional organic solvents, or polymers. When the above composite fine particles are dispersed in a medium, light scattering in the visible light region takes place at the interface of the composite fine particles and the medium, whereby the transparency of the composition is drastically lowered. However, there has been conventionally no technical ideas of controlling the refractive index of the ultraviolet shielding particle of the composite fine particles.

In the fields of resin fillers, fluorine-based inorganic compounds, such as $MgF_2$ and $CaF_2$, or fluorine-based organic polymers, such as polyethylene tetrafluoride, which are known as low-refractive index materials having high transparency, are added to powders, etc. as starting materials to lower their refractive indices.

For instance, Japanese Patent Laid-Open No. 4-85346 discloses a glass powder, used as a transparent inorganic powder for resin fillers, comprising metal oxides, such as $SiO_2$, $Al_2O_3$, $B_2O_3$, BaO, SrO, ZnO, and MgO, and metal fluorides, the glass powder having a refractive index (Nd) adjusted in the range of from 1.44 to 1.70. The publication discloses that since the glass powder has a high light transmittance and does not show strong alkalinity, the resins do not undergo any substantial denaturalization, and have significantly low instability in resin hardening. However, the publication merely discloses that a highly transparent inorganic powder for resin fillers is obtainable by changing the compositional ratio of the materials, and the above metal oxides, etc. are not present in the state of particles in the final product powder owing to the high-temperature melting production process, and this publication never mentions about the ultraviolet shielding ability. Further, this publication does not at all disclose that the composite fine particles comprising aggregates of two or more kinds of fine particles as in the present invention have the compositional dependency with respect to an average refractive index of the composite fine particles, nor does it have any such technical ideas.

In order to solve various problems inherent in the ultraviolet shielding agents mentioned above, the present inventors have previously developed ultraviolet shielding composite fine particles, method for producing the same, and cosmetics (WO 95/09895 Publication). In the publication, an ultraviolet shielding agent having high transparency in the visible light and high ultraviolet shielding ability was developed by combining fine particles (daughter particles) having the ultraviolet shielding ability with fine particle aggregates (matrix particles) in which the daughter particles are dispersed and incorporated, and by determining combinations of the two components according to the difference of their band gap energies, and thereby the optical properties of the ultrafine particles can be optimized. This ultraviolet shielding agent is characterized, besides the features mentioned above, in that, since the refractive indices can be controlled in a wide range by changing the materials of matrix/daughter particles and proportions thereof, high transparency can be exhibited even when dispersed in various media, and high transparency can be exhibited regardless of their shapes. Also, easy handling (transportation, surface treatment, formulation, etc.) is achieved owing to the size of the level of fine particles, and they are usable for cosmetics since they do not change the color tone.

However, this ultraviolet shielding agent is yet to be improved in the following:
(1) In the case where a particularly high ultraviolet shielding ability is desired in the use for cosmetics, the amount of the ultraviolet shielding agent has to be made large. In this case, an upper limit of the amount of the ultraviolet shielding agent has to be set so as not to impair the skin texture of the cosmetics due to the texture of the composite fine particle powder itself.
(2) Also, in the case of using the ultraviolet shielding agent for cosmetics, the catalytic activities of ultrafine particles located near the surfaces of the composite fine particles have to be suppressed. In general, the suppression of the catalytic activities may be achieved by coating the surfaces of the composite fine particles with an inorganic material having substantially no catalytic activities. However, on the other hand, when coated with an inorganic material, the proportion of the daughter particles in the coated composite fine particles is lowered, which in turn may cause a problem that the ultraviolet shielding ability per unit weight of the composite fine particles comprising a surface coat may be lowered depending upon the thickness of the surface coat.
(3) Further, the composite fine particles disclosed in WO 95/09895 are obtainable in the powder form by drying droplets of the starting material liquid mixture comprising the matrix particles and the daughter particles, and by thermal decomposition. Even when the above powdery composite fine particles are surface-coated with inorganic materials, etc., only the surfaces of the composite fine particles are coated. Therefore, when the composite fine particles undergo pulverization or disintegration in various applications, the uncoated inner portions of the composite fine particles are liable to be exposed, so that the suppression of the catalytic activities is liable to be insufficient.

DISCLOSURE OF THE INVENTION

The present invention is to solve the various problems in the ultraviolet shielding agents described above. Specifically, objects of the present invention are to provide ultraviolet shielding composite fine particles whose amounts can have a wider degree of freedom when formulated in cosmetics, the composite fine particles maintaining the effective proportion of the daughter particles, having substantially no catalytic activities even when subjected to pulverization or disintegration, being uniformly and stably dispersed in a medium (for example, cosmetics and paints), having a high transparency in the visible light region and high shielding ability in the ultraviolet light region, and permitting easy handling; methods for producing the same; and cosmetics using the same.

The present inventors have intensively studied to solve the various problems mentioned above. As a result, they have found the following:
(1) Regarding the problem of causing the limitation of the ultraviolet shielding ability owing to the compositional upper limit of the composite fine particles, the texture of the powder can be lowered by having an even smaller average particle size of the ultraviolet shielding composite fine particles, and the compositional upper limit of the composite fine particles can be increased, thereby succeeding in enjoying a remarkably wider compositional degree of freedom. In this case, although the method disclosed in WO 95/09895 Publication is suitable for the production of the composite fine particles having a relatively large average particle size, it is not suitable for efficiently producing composite fine particles with a very fine size of a level of about 0.5 μm or less. Therefore, the present inventors have found out a novel production method comprising the steps of preparing a liquid mixture containing a mixture of the matrix particle starting material and the daughter particle starting material; subjecting the liquid mixture to a mill treatment and/or a high-pressure dispersion treatment, to form composite fine particles in a liquid phase comprising aggregates of daughter particles/matrix particles. By using this method, the average particle size of the composite fine particles can be easily made even smaller, so that the skin texture of the powder can be lowered and the compositional upper limit of the composite fine particles can be increased, thereby succeeding in enjoying a remarkably wider compositional degree of freedom.

(2) Further, in order to suppress the catalytic activities of the composite fine particles, the present inventors have found that instead of coating the surfaces of the composite fine particles with the inorganic material having substantially no catalytic activities, the surfaces are directly coated with a silicone which is a surface treatment agent giving a water-repellent ability, by which the catalytic activities of the composite fine particles can be unexpectedly substantially suppressed. Therefore, by coating the surface of the composite fine particles with a silicone, the surrounding medium of the composite fine particles is for practical purposes not deteriorated by the catalytic activities or the photocatalytic activities. Also, by coating the surfaces with the silicone, an oily medium and the surfaces of the composite fine particles become more compatible, and by the steric hindrance by the silicone, the dispersibility of the composite fine particles in the oil becomes good, so that the high transparency of the visible light and the high shielding ability of the ultraviolet light are liable to be easily exhibited. Also, since no surface coatings are formed by inorganic materials, the proportion of the daughter particles in the composite fine particles is kept high, thereby resulting in an increase in the ultraviolet shielding ability per unit weight of the composite fine particles.

(3) Furthermore, the present inventors have found a method for carrying out a silicone coating onto the composite fine particles in a liquid phase. In this case, since a coating treatment with a silicone is carried out while maintaining a dispersion state in a liquid phase of the composite fine particles formed in a liquid phase, the silicone is assumed to be present not only on the surface of the fine composite particles but also in the inner portion of the composite fine particles, so that the surface of the primary particles, such as daughter particles, are presumably coated to some degree. Therefore, even when the composite fine particles coated with the silicone are subjected to disintegration, the resulting particles are substantially coated with the silicone, so that the suppression of the catalytic activities is not liable to be lost.

Also, the present inventors have found that when the silicone coating is carried out, the coating treatment in a liquid phase can be easily carried out particularly when using modified silicones, reactive silicones, or silicone-modified copolymers, and that the particles obtained after the coating treatment and the silicone have a strong coating strength, thereby being remarkably effective therefor.

Specifically, in sum, the present invention is concerned with the following:

(1) Ultraviolet shielding composite fine particles having transparency in a visible light region, comprising matrix particles comprising an aggregate of primary particles having an average particle size of from 0.001 to 0.3 $\mu$m, the aggregate being formed while the primary particles retain their shapes; and daughter particles having an average particle size of from 0.001 to 0.1 $\mu$m, the daughter particles being dispersed in and supported by the matrix particles, wherein the daughter particles have a smaller band gap energy than the particles constituting the matrix particles and are capable of absorbing ultraviolet light, and wherein the surfaces of the composite fine particles are coated with one or more silicones selected from the group consisting of modified silicones, reactive silicones, and silicone-modified copolymers, and wherein the ultraviolet shielding composite fine particles have substantially no catalytic activities;

(2) An oil dispersion of the ultraviolet shielding composite fine particles as defined in item (1) above, obtainable by the steps of:
  (a) preparing a liquid mixture comprising starting materials for matrix particles which are one or more materials selected from the group consisting of sols containing particles constituting matrix particles and powders of the matrix particles, the matrix particles having a primary particle with an average particle size of from 0.001 to 0.3 $\mu$m; and starting materials for daughter particles which are one or more materials selected from the group consisting of sols containing daughter particles and powders of the daughter particles, the daughter particles having an average particle size of from 0.001 to 0.1 $\mu$m, and treating the liquid mixture in a mill and/or an apparatus for high-pressure dispersion, to thereby produce composite fine particles wherein the daughter particles/matrix particles are aggregated in a liquid phase;
  (b) coating the composite fine particles produced in step (a) with one or more silicones selected from the group consisting of modified silicones, reactive silicones, and silicone-modified copolymers; and
  (c') dispersing in an oil the composite fine particles coated with the silicone obtained in step (b);

(3) A method for producing ultraviolet shielding composite fine particles comprising matrix particles and daughter particles, the daughter particles being dispersed in and supported by the matrix particles, the ultraviolet shielding composite fine particles having substantially no catalytic activities and having transparency in a visible light region, the method comprising the steps of:
  (a) preparing a liquid mixture comprising starting materials for matrix particles which are one or more materials selected from the group consisting of sols containing particles constituting matrix particles and powders of the matrix particles, the matrix particles having a primary particle with an average particle size of from 0.001 to 0.3 $\mu$m; and starting materials for daughter particles which are one or more materials selected from the group consisting of sols containing daughter particles and powders of the daughter particles, the daughter particles having an average particle size of from 0.001 to 0.1 $\mu$m, and then treating the liquid mixture in a mill and/or an apparatus for high-pressure dispersion, to thereby produce composite fine particles wherein the daughter particles/matrix particles are aggregated in a liquid phase; and
  (b) coating the composite fine particles produced in step (a) with one or more silicones selected from the group consisting of modified silicones, reactive silicones, and silicone-modified copolymers; and (4) Cosmetics comprising ultraviolet shielding composite fine particles as defined in item (1) or item (2).

BEST MODE FOR CARRYING OUT THE INVENTION

Figure 1:
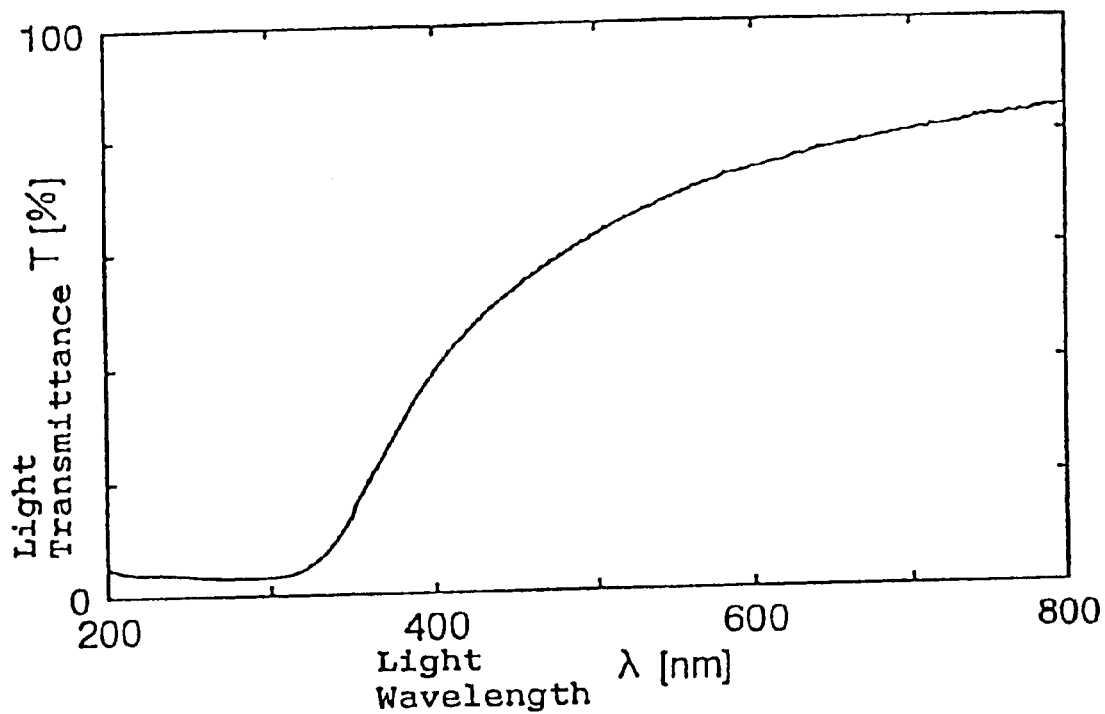
FIG. 1 is a chart showing the measurement results of the light transmittance of the ultraviolet shielding composite fine particles obtained in Example 1, as measured by an ultraviolet-visible light spectrophotometer.

Fine particles having a relatively small particle size and having a high shielding ability against ultraviolet light are likely to form aggregates, so that it is difficult to disperse them in a medium to reveal their shielding function well. Therefore, by the formation of a composite of the fine particles with relatively large particles, namely by supporting the fine particles as daughter particles in matrix particles used as a carrier, the fine particles are maintained in a good dispersion state, thereby retaining their high shielding ability against the ultraviolet light. Further, by coating the surface of the composite fine particles with silicones, the catalytic activities of the composite fine particles can be substantially suppressed. In other words, by coating the surface of the composite fine particles with silicones, the medium surrounding the composite fine particles is not liable to undergo deterioration by the catalytic activities or photocatalytic activities of the particles. Furthermore, the ultraviolet shielding composite fine particle powder is obtainable by the step of drying and/or pulverizing the composite fine particles coated with the silicones. Alternatively, an oil dispersion of the ultraviolet shielding composite fine particles is also obtainable by the step of dispersing the composite fine particles coated with the silicones in an oil medium. In the present specification, the matrix particles of the composite fine particles refer to a matrix containing and supporting daughter particles dispersed therein. The matrix particles are formed as aggregates while retaining the shapes of the particles constituting the matrix particles (i.e., primary particles). The daughter particles refer to particles having an ultraviolet shielding ability, other than the matrix particles.

1. Preferred embodiments of the composite fine particles of the present invention will be explained in detail below from the aspect of a band gap energy of the particles, refractive indices of the composite fine particles, grain boundaries of the particles, and coatings formed on the surfaces of the composite fine particles by silicones.

(1) Band gap energy of particles

In the composite fine particles of the present invention, the fine particles used as the daughter particles have to have a good shielding ability in the ultraviolet light region. The ultraviolet shielding abilities are classified into absorbing ability of ultraviolet light and scattering ability of ultraviolet light. The ultraviolet light absorption by inorganic compounds is ascribed to exciton absorption of mainly semiconductive compounds, and compounds having a band gap energy of from 3.0 to 4.0 eV effectively show such a property. The scattering ability of ultraviolet light is intensely exhibited as Mie scattering. In the case of high-refractive index materials, such as $TiO_2$, scattering is remarkably observed when the particle size of the material is about one-half the wavelength of the ultraviolet light, namely 0.2 $\mu$m or less.

Since in ceramics the valence electron band and the conduction band are not continuous, ceramics are known to absorb light having a wavelength corresponding to an energy not less than the band gap energy, the band gap energy referring to the difference between the energy levels of the two bands mentioned above. For instance, ZnO has a band gap energy of 3.2 eV, which absorbs light having a wavelength of not more than 390 nm. The inorganic ultraviolet shielding agent absorbs ultraviolet light because its band gap energy corresponds to the wavelength of the ultraviolet light.

Therefore, in the composite fine particles of the present invention, in order for the daughter particles to effectively exhibit scattering ability and absorption ability of the ultraviolet light, the particles constituting the matrix particles must have a band gap energy larger than that of the daughter particles. For instance, in the case of using aggregates of $TiO_2$ particles (rutile-type) as the matrix particles, when ZnO fine particles having a band gap energy smaller than that of $TiO_2$ are contained as the daughter particles, the ultraviolet light having a wavelength of not more than 320 nm is absorbed by exciton absorption corresponding to the band gap energy of the particles constituting the matrix particles ($TiO_2$). Also, the ultraviolet light having a wavelength in the vicinity of 350 nm, which penetrates the matrix particles without being absorbed, is absorbed by exciton absorption corresponding to the band gap energy of the daughter particles while being multiply scattered by the daughter particles. Accordingly, the ultraviolet light having a wavelength of not more than 350 nm can be shielded. By contrast, in the case where $TiO_2$ is used as the particles constituting the matrix particles, when $SnO_2$ fine particles having a larger band gap energy than $TiO_2$ are used as the daughter particles, the ultraviolet light having a wavelength of not more than 320 nm is absorbed by exciton absorption corresponding to the band gap energy of the $TiO_2$ particles. However, the ultraviolet light having a wavelength in the vicinity of 350 nm, which penetrates the matrix particles without being absorbed, is not absorbed by exciton absorption corresponding to a band gap energy of $SnO_2$. Accordingly, the composite fine particles cannot provide good shielding effects against the ultraviolet light having wavelengths in the vicinity of 350 nm.

From the above-raised points, in the composite fine particles of the present invention, the particles constituting the matrix particles have a band gap energy of preferably 3 to 9 eV, more preferably 5 to 9 eV. In order to more securely have the ultraviolet light reach the daughter particles, the minimum band gap energy of the daughter particles is smaller than that of the band gap energy of the particles constituting the matrix particles preferably by not less than 0.2 eV, the ultraviolet light having wavelengths at which absorption and scattering of the ultraviolet light can be achieved by the daughter particles (2) Refractive indices of composite fine particles When the ultraviolet shielding composite fine particles are actually used, it is necessary for them to exhibit high transparency in the visible light region while maintaining a high shielding ability in the ultraviolet light region. Here, (i) in order to maintain a high shielding ability, the difference between the refractive indices of the matrix particles and the daughter particles has to be kept large because the ultraviolet shielding ability is improved when the difference between the refractive indices is large. In the present invention, the difference therebetween is preferably not less than 0.1. For this reason, in the present invention, metal oxides and fluorine compounds having relatively low-refractive indices are used as materials constituting the matrix particles together with the daughter particles having a relatively high refractive index. Also, (ii) in order to exhibit high transparency, upon considering the difference with the surrounding materials (medium), the difference between the refractive indices of the composite fine particles and the medium has to be kept as small as possible. Thus, the refractive index of the composite fine particles has to be controlled in order to make the difference small. The present invention is characterized by controlling the refractive indices by using a fluorine compound.

In a suspension of the composite fine particles (namely a state to be used for cosmetics, etc.), when the refractive index of the composite fine particles differs largely from that of the medium, transparency is likely to be lost because the visible light is refracted or reflected at the interface of the composite fine particles and the medium. Here, the refractive index may be measured by a generally known immersion method (see Toshiharu Takou, et al., Optical Measurement Handbook, p. 475, 1981, published by Asakura Publishers). Here, the refractive index of the sample is the refractive index of a medium, whose highest light transmittance is obtained at a wavelength of 589.3 nm. However, the operating procedure for the immersion method is complicated, and time-consuming. For simplicity, the refractive index can be theoretically calculated from the refractive indices of the daughter particles and the primary particles of the matrix particles and the volume ratio therebetween. Since the theoretically calculated refractive index closely approximates data obtained by the immersion method depending on the composite fine particles, the refractive indices of the composite fine particles can be also obtained by a simple method as mentioned above. The refractive index $n_D^{20}$ of the generally used medium is from 1.3 to 1.8. On the other hand, since many of metal oxides having a high ultraviolet shielding ability, such as $TiO_2$ and ZnO, have a refractive index $n_D^{20}$ of not less than 2.0, when the metal oxides are used as the daughter particles, the refractive index of the composite fine particles has to be approximated to that of the medium by using a low-refractive index material for the matrix particles. Specifically, an average refractive index of the composite fine particles is from 1.3 to 2.5, preferably from 1.3 to 2.0, more preferably from 1.3 to 1.8, particularly preferably from 1.3 to 1.7, and most preferably from 1.4 to 1.5. Also, a difference of the refractive indices between the matrix particles and the daughter particles in the composite fine particles of the present invention is preferably not less than 0.1. By keeping the difference to the above range, the scattering ability of the ultraviolet light is improved.

(3) Grain boundaries of particles

From the aspect of grain boundaries, as the particle size of the primary particles of the matrix particles becomes smaller, namely as the grain boundaries in the inner portion of the matrix particles become smaller, the visible light cannot detect the presence of the fine grain boundaries, so that the matrix particles are provided with transparency regardless of the crystallinity of the primary particles of the matrix particles. Since the daughter particles which comprise ultrafine particles also have good transparency, the composite fine particles as a consequence have good transparency.

(4) Coatings formed on the surface of the composite fine particles by silicones

In the case of coating the surfaces of the composite fine particles with a silicone in order to suppress the catalytic activities of the ultrafine particles, the thickness of the coating layer is considered to be sufficient if the active sites on the surfaces of the composite fine particles are substantially coated so as to prevent the surface activities from affecting the surrounding medium of the composite fine particles. In other words, by substantially suppressing the surface activities of the composite fine particles, the deterioration of the medium contacting the surfaces of the composite fine particles (the media being, for instance, cosmetic base materials, paints, etc.), can be prevented. Also, the dispersibility of the composite fine particles can be stably maintained for a long period of time. While the above are conventionally unavoidable problems in cases where inorganic materials are dispersed in various kinds of media, the present invention provides a means for solving the conventional problems.

2. Next, the method for producing the ultraviolet shielding composite fine particles of the present invention will be explained according to each of the steps described below.

The production methods of the present invention have the two embodiments: (1) One embodiment where the composite fine particles are powdered by drying and/or pulverization; and (2) another embodiment where the composite fine particles are dispersed in an oil agent. Each of the embodiments comprises the following three steps.

(1) Embodiment where the composite fine particles are powdered by drying and/or pulverization, comprising the steps of:

(a) preparing a liquid mixture comprising starting materials for matrix particles which are present in one or more forms selected from the group consisting of sols containing particles constituting matrix particles and powders of the matrix particles, the matrix particles having a primary particle with an average particle size of from 0.001 to 0.3 µm; and starting materials for daughter particles which are present in one or more forms selected from the group consisting of sols containing daughter particles and powders of the daughter particles, the daughter particles having an average particle size of from 0.001 to 0.1 µm, and treating the liquid mixture in a mill and/or an apparatus for high-pressure dispersion, to thereby form composite fine particles comprising aggregates of the daughter particles/matrix particles in a liquid phase;

(b) coating the composite fine particles obtained in step (a) with one or more silicones selected from the group consisting of modified silicones, reactive silicones, and silicone-modified copolymers; and (c) drying and/or pulverizing the composite fine particles coated with the silicone obtainable in step (b).

(2) Embodiment where the composite fine particles are dispersed in an oil agent, comprising the steps of:

(a) preparing a liquid mixture comprising starting materials for matrix particles which are present in one or more forms selected from the group consisting of sols containing particles constituting matrix particles and powders of the matrix particles, the matrix particles having a primary particle with an average particle size of from 0.001 to 0.3 µm; and starting materials for daughter particles which are present in one or more forms selected from the group consisting of sols containing daughter particles and powders of the daughter particles, the daughter particles having an average particle size of from 0.001 to 0.1 μm, and treating the liquid mixture in a mill and/or an apparatus for high-pressure dispersion, to thereby form composite fine particles comprising aggregates of the daughter particles/matrix particles in a liquid phase;

(b) coating the composite fine particles obtainable in step (a) with one or more silicones selected from the group consisting of modified silicones, reactive silicones, and silicone-modified copolymers; and (c') dispersing in an oil agent the composite fine particles coated with the silicone obtainable in step (b).

In the preparation of the liquid mixture in step (a) and the formation step of the composite fine particles above, in the case of using of ultrafine particles having an average particle size of from 0.001 to 0.1 μm as the daughter particles, the daughter particle powder is desirably disintegrated or pulverized in a mill or an apparatus for high-pressure dispersion, whereby the dispersion state of the daughter particles in the liquid mixture is maintained. Examples of mills include bead mills, sand mills, ball mills, and agitation mills, and examples of high-pressure dispersion devices include microfluidizers and nanomizers. Here, in the case where the daughter particles comprising the above ultrafine particle powder is used, and a liquid mixture having a large proportion and high concentration of the daughter particles are subjected to a mill treatment and/or a high-pressure dispersion treatment, a primary treatment is preferably carried out prior to the above treatments using a dispersion device capable of disintegrating powders of the ultrafine particles, the dispersion devices including homomixers and homogenizers. The reasons for carrying out the primary treatment are as follows. By disintegrating the powders of the ultrafine particles which are in an aggregated state at a high concentration, the load for the disintegration and dispersion required in secondary treatments subsequent to the above treatment, namely a mill treatment step and/or a high-pressure dispersion treatment step, is reduced, so that the disintegration and dispersion can be efficiently carried out.

The composite fine particles comprising aggregates of the daughter particles/matrix particles are produced in the liquid phase by these treatments. In this step, the composite fine particles are dispersed in the liquid phase, wherein the daughter particles/matrix particles in an aggregate state are mainly bound by electric forces and partially by weak van der Waal's force. Therefore, since the composite fine particles are not in a powder state as the composite fine particles disclosed in WO95/09895, the daughter particles are not firmly supported by the matrix particles. Thus, when a surface-coating with a silicone is carried out in the subsequent step, the silicones not only coat the surfaces of the composite fine particles but they are incorporated in the composite fine particles, so that the surfaces of the primary particles, such as the daughter particles, are presumably coated to some degree.

Also, in step (b), which is a coating step by silicones, it is preferred to employ a method for coating with silicones by dispersing the composite fine particles in the liquid phase obtained in step (a) in a solvent having a compatibility with the silicone.

The silicones usable in the present invention include one or more silicones selected from the group consisting of modified silicones, reactive silicones, and silicone-modified copolymers.

Examples of the modified silicones include polyether-modified silicones, alkyl-aralkyl-modified silicones, alkyl-aralkyl-polyether-modified silicones, alkyl-higher alcohol-modified silicones, alcohol-modified silicones, fluoro-modified silicones, long-chained alkyl-modified silicones, fluoroalkyl-modified silicones, and alkylene oxide-modified silicones.

Examples of the reactive silicones include amino-modified silicones, amino-polyether-modified silicones, epoxy-modified silicones, epoxy-polyether-modified silicones, carboxyl-modified silicones, carboxyl-polyether-modified silicones, carbinol-modified silicones, mercapto-modified silicones, phenol-modified silicones, oxazoline-modified silicones, hydrogen-modified silicones, vinyl-modified silicones, and hydroxy-modified silicones.

Examples of the silicone-modified copolymers include alkylene oxide-modified copolymers, silphenylene-modified copolymers, ethylene-modified copolymers, α-methylstyrene-modified copolymers, carboran-modified copolymers, bisphenol A carbonate-modified copolymers, diphenylsiloxane polyborate, alkoxysilane-modified polymers, and polyalkoxysilanes.

Among the silicones mentioned above, particularly when used for application as cosmetics, from the aspect of safety to skins and coating strength to the particles, preference is given to the oxazoline-modified silicones and the amino-modified silicones, particularly to the oxazoline-modified silicones.

Incidentally, methods of employing methyl hydrogen polysiloxanes may be used as a method for coating with silicones. Since the coating strength is weak when simply adsorbing methyl hydrogen polysiloxanes, such steps as drying and baking are normally required thereafter. However, the composite fine particles obtained after the baking step as mentioned above are in the state of aggregated fine particles, so that its ultraviolet absorbing ability or transparency in the visible light is lowered. Also, the photocatalytic activities are caused when the aggregated particles are disintegrated.

Next, in step (c) of drying and/or pulverizing the composite fine particles coated with the silicone, the drying methods and the pulverization methods are not particularly limited. For example, as drying methods, such methods as hot-air drying and topping treatments may be employed, and in the pulverization method, such means as sand mills and blade-type mills may be employed. The composite fine particles obtained after the pulverization step may be controlled to a given particle size by classification. In order to determine the particle size and shapes of the resulting composite fine particles, an electron microscope may be used.

Next, in step (c') where the composite fine particles are dispersed in an oil agent, the methods for dispersing the composite fine particles in an oil agent are not particularly limited. For instance, after mixing the oil agent and the liquid mixture dispersion containing the silicone-coated composite fine particles, such treatments as a topping treatment may be carried out in the case where the liquid dispersion is volatile, as in the case of ethanol. Alternatively, conventional solvent substitution methods may be employed in the case where the liquid dispersion is non-volatile.

3. Each of the starting materials used in the production methods of the present invention will be explained below.

(1) Daughter particles

The daughter particles constituting the composite fine particles in the present invention have good transparency in the visible light region while having a good shielding ability in the ultraviolet light region. In other words, the daughter particles are required not to absorb the light in the visible light region and to have a size of the level small enough not to scatter the visible light.

In order to satisfy the requirements of not absorbing the light in the visible light region but absorbing the ultraviolet light, the materials constituting the daughter particles preferably have a wavelength for an exciton absorption of a band gap energy corresponding to the wavelengths in the ultraviolet light region. Specifically, semiconductive compounds having a band gap energy of from 3.0 to 4.0 eV are preferred, including, for instance, $TiO_2$, $ZnO$, $CeO_2$, $SiC$, $SnO_2$, $WO_3$, $SrTiO_3$, $BaTiO_3$, and $CaTiO_3$, which characteristically exhibit the above property. Among them, $TiO_2$, $ZnO$, and $CeO_2$ are generally well used as ultraviolet shielding agents, and one or more members selected from the group consisting of these compounds are particularly preferred. In particular, in order to shield the light up to the ultraviolet light region A (320 to 400 nm), $ZnO$ and $CeO_2$ are effectively used. Also, in order to shield the light of the ultraviolet light region B (280 to 320 nm), $TiO_2$ is effectively used. Incidentally, in order to shield both the light of the ultraviolet light region B and that of the ultraviolet light region A, the daughter particles may be those in which $TiO_2$ and one or more members selected from the group consisting of $ZnO$, $CeO_2$, $BaTiO_3$, $CaTiO_3$, $SrTiO_3$, and $SiC$ are preferably used.

Alternatively, in the case where $TiO_2$ is used, the shielding region can be extended to the ultraviolet light region A by incorporating, as impurity dopes, an element having a valence number of 5 or more, such as W, P, Ta, Nb, Sb, or Mo, or an element having a valence number of 3 or less, such as Zn, Al, Mg, and Ca.

The shapes of the daughter particles are not particularly limited, which may be spherical, plate-like or acicular. The particle size of the daughter particles is preferably substantially the same as the particle size of the primary particles of the matrix particles from the viewpoint of giving good dispersion state of the daughter particles in the matrix particles. Furthermore, as for the scattering ability of the ultraviolet light, which is intensely exhibited by Mie scattering, scattering can be remarkably noted when the particle size is about one-half the wavelength of the ultraviolet light, namely, not more than 0.2 μm. Therefore, in order to satisfy both good transparency in the visible light region and good shielding ability in the ultraviolet light region, the daughter particles have an average particle size of preferably not more than 0.2 μm, more preferably not more than 0.1 μm, particularly 0.001 to 0.1 μm, and more particularly not more than 0.05 μm. In the present invention, the term "daughter particles" refers to primary particles which are alone dispersed in and supported thereby and/or aggregates of the primary particles. Therefore, the average particle size of the daughter particles may also mean the average particle size of the aggregates.

In the present invention, since the daughter particles are present preferably in a dispersed state in the inner portion of the composite fine particles, higher dispersibility and stability of the daughter particles in a sol are desired. In order to achieve this, the surfaces of the daughter particles may be coated with other materials, or the daughter particles may be blended with a sol stabilizer. For instance, in the case where $TiO_2$ ultrafine particles are used as the daughter particles, the surfaces of the ultrafine particles may be coated with such compounds as $SiO_2$ and $Al_2O_3$ to improve dispersibility. Alternatively, the ultrafine particles may be blended with a basic stabilizer, such as $NH_3$, to stabilize the state of the $TiO_2$ sol. Also, in the case where the ultrafine particle powder is surface-improved to achieve good dispersion, they can be used as starting materials for the daughter particles. Therefore, as for the fine particles usable as the daughter particles, those surface-treated with inorganic materials comprising at least one member selected from silica, alumina, and zirconia; those surface-coated with organic materials comprising organosiloxanes, lauric acid, stearic acid, alkoxysilanes; and those surface-coated with a combination of those inorganic materials and organic materials may be usable. Incidentally, the daughter particles surface-treated as described above are liable to have lowered catalytic activities, thereby making it possible to utilize them for the ultraviolet shielding composite fine particles for having substantially no catalytic activities. The sol used in the present invention refers to fluids containing particles which cannot be generally observed by an ordinary microscope but having a particle size larger than that of an atom or that of a low molecular compound (see Iwanami Dictionary of Physics and Chemistry, Third Edition, published by Iwanami Publishers). Examples of sols include hydrosols of silica and suspensions of $TiO_2$ ultrafine particles.

(2) Matrix particles

The matrix particles constituting the composite fine particles must satisfy the transparency in the visible light region is the same manner as the daughter particles in order to exhibit good transparency to the composite fine particle suspension. Specifically, it is desired that the matrix particles are constituted by materials which do not absorb the visible light, and that the primary particles of the matrix particles preferably have a particle size not exceeding 0.3 μm. For instance, a preference is given to aggregates of the ultrafine particles, each of the ultrafine particles having an average particle size of 0.01 μm.

As for the materials constituting the matrix particles, materials having high transparency, may be those comprising metal oxides and/or fluorine compounds. For instance, metal oxides, mixtures of metal oxides and fluorine compounds, or fluorine compounds alone may be used. Since the aggregates of the fine particles usually constitute the matrix particles, the fine particles constituting the aggregates (i.e. primary particles) have an average particle size of not more than 0.2 μm, specifically from 0.001 to 0.2 μm, in order to satisfy the requirements for the matrix particles as mentioned above. Particularly, a preference is given to particles having an average particle size of not more than 0.15 μm, more preferably not more than 0.1 μm, still more preferably not more than 0.05 μm. For the same reasons as those for the daughter particles, the surfaces of the particles constituting the matrix particles may be coated with other materials, or the fine particles may be blended with sol stabilizers. Here, the coating materials or the stabilizers used may be similar to those used for the daughter particles.

Many of the metal oxides are available in the form of chemically stable solids, so that the metal oxides can be suitably used for materials constituting the matrix particles. Examples of the metal oxides contained in the matrix particles include $TiO_2$, $CuO$, $ZnO$, $MgO$, $CeO_2$, $SnO_2$, $SiO_2$, $Fe_2O_3$, $Al_2O_3$, $NiO_2$, and $MnO_2$. A preference is given to $SiO_2$ and $Al_2O_3$ from the viewpoint of having a suitable refractive index and good transparency as explained above. Also, a preference is given to fine particles of $SnO_2$, $In_2O_3$, $SiO_2$, and $ZnO$, from the viewpoint of using ceramic fine particles having large band gap energies.

Many of the fluorine compounds contained in the matrix particles are chemically stable and have a low refractive index, so that the compounds are highly useful for controlling the refractive index of the resulting composite fine particles. The fluorine compounds include those present in solid or liquid state at an ambient temperature. Examples of such solid inorganic fluorine compounds at an ambient temperature include $MgF_2$, $CaF_2$, $AlF_3$, LiF, $NiF_2$, and $BaF_2$. Examples of organic fluorine compounds include fluororesins, such as polytetrafluoroethylene (hereinafter abbreviated as "PTFE"), tetrafluoroethylene-hexafluoropropylene copolymers, tetrafluoroethylene-ethylene copolymers, vinylidene polyfluorides, and vinyl polyfluorides. Among them, when the fluorine compound is $MgF_2$ and/or polytetrafluoroethylenes, it is suitable from the viewpoint of the refractive index and transparency.

The average particle size of the fluorine compounds in solid state at room temperature is preferably not more than 0.3 μm, more preferably not more than 0.2 μm. The reason therefor is that when the average particle size exceeds 0.3 μm, the aggregating forces among the particles become weak, thereby lowering the strength of the composite fine particles.

Examples of liquid fluorine compounds at an ambient temperature include perfluoropolyethers (hereinafter abbreviated as "PFPE"). An example of PFPE may be, for instance, perfluoropolymethylisopropylethers (for instance, "FOMBLIN HC", manufactured by Nikko Chemicals K.K.). The PFPE mentioned above is useful not only for lowering the refractive index of the composite fine particles but also for providing moisture with smooth skin texture, so that the PFPE is highly suitable as fine particles for use in cosmetics. When the liquid fluorine compounds mentioned above are used, a solvent must be properly selected so as not to cause phase separation of the daughter particle starting materials and the matrix particle starting materials in the solvent. However, when the solvent is water, an emulsion comprising liquid fluorine compounds at room temperature which are emulsified by various kinds of surfactants may be preferably used. For instance, an emulsion of perfluoropolyether (oil-in-water type) may be used. The emulsion size is preferably of a size not more than 0.1 times that of the liquid droplets. When the emulsion size exceeds 0.1 times that of the liquid droplets, the emulsion becomes larger than the formed particles, and thereby the production of particles becomes difficult.

As described above, in the present invention, the liquid fluorine compounds at an ambient temperature may be also used as materials having low refractive indices. In this case, the liquid fluorine compounds may be used together with the metal oxides and/or the solid fluorine compounds at an ambient temperature in order to increase freedom in the refractive index control.

Regarding suitable combinations of the daughter particles and the matrix particles in the present invention as described above, a preference is given to cases where the daughter particles comprise $TiO_2$ and/or ZnO; the matrix particles comprise $SiO_2$ and/or $Al_2O_3$; the silicones used in the coating treatment comprise modified silicones, reactive silicones and silicone-modified silicones, with a particular preference given to the oxazoline-modified silicones and the amino-modified silicones, from the viewpoints of providing safety, stability, and ultraviolet shielding effects.

In the present invention, materials other than the metal oxides and the fluorine compounds mentioned above may be included in the daughter particles and the matrix particles. For example, stabilizers of the starting material sol or a coating agent for sol particles, etc. may be contained as long as the optical properties of the composite fine particles are not impaired.

4. Next, the preparation of the starting material liquid mixture using the starting materials mentioned above and the method for producing the composite fine particles will be explained in more detail below.

When the liquid mixture of the starting materials is prepared, it is important to uniformly disperse and blend the liquid mixture containing the starting materials for the daughter particles and the starting materials for the matrix particles, so as to easily disperse the daughter particles in the matrix particles. By thoroughly blending the starting materials for the daughter particles and the starting materials for the matrix particles, the daughter particles can be present on the surfaces of and/or in the inner portions of the matrix particles. At this time, fine particles comprising starting materials of daughter particles and those of matrix particles are gathered by electrostatic forces, to form aggregated composite fine particles. For instance, in the case where $TiO_2$ ultrafine particle powder is selected as the starting material for the daughter particles and an $SiO_2$ sol (aqueous; "ST-C," manufactured by Ishihara Sangyo; pH 8.5 to 9.0) is selected as the starting materials for the matrix particles, and the liquid mixture of the above starting materials are subjected to a mill treatment or a high-pressure dispersion treatment under suitable conditions, $TiO_2$ (an isoelectric point being pH of about 5 to 7) is negatively charged, and $SiO_2$ (electric, double-layered surfaces) is positively charged, so that fine particles are formed as aggregates of the daughter particles and the matrix particles being bound by electrostatic forces between $TiO_2$, the daughter particles and $SiO_2$, the matrix particles. Also, in another case where ZnO ultrafine particle powder is selected as the starting material for the daughter particles and an $SiO_2$ sol (aqueous; "ST-C," manufactured by Ishihara Sangyo; pH 8.5 to 9.0) is selected as the starting materials for the matrix particles, and where the above starting materials are subjected to a mill treatment or a high-pressure dispersion treatment under suitable conditions, ZnO is positively charged, and an $SiO_2$ surface is negatively charged, so that the composite fine particles are formed as aggregates of the daughter particles and the matrix particles which are bound by electrostatic forces between ZnO, the daughter particles, and $SiO_2$, the matrix particles. Incidentally, in this case, a slidable surface in the electric double layer of $SiO_2$ is presumably cracked whereby the surface is negatively charged.

The $SiO_2$ sols which are used in the above examples have the following functions: (1) They act as a medium for efficiently disintegrating daughter particles which are usually present in an aggregated state to about the size of the primary particles; (2) they form a backbone of the matrix particles to which the daughter particles are adhered simultaneously therewith; and (3) they act as a dispersant for inhibiting the aggregation of the composite fine particles with each other by electrostatic repulsion of $SiO_2$ on the surface of the composite fine particles after formation of the composite fine particles. Here, particle size of the $SiO_2$ sol may be suitably selected according to functions (1) to (3) described above. For instance, in the case where function (3) is considered to be very important, the particle size of the $SiO_2$ sol is preferably of about the same level as or less than the particle size of the daughter particles. Specifically, the particle size of the $SiO_2$ sol is suitably not more than 0.1 μm, preferably not more than 0.05 μm, more preferably not more than 0.02 μm. Incidentally, the solvents used for the $SiO_2$ sol include hydrosols (aqueous) and organosols, which may be suitably selected taking into consideration the kinds of the daughter particles and the dispersion stability.

According to the methods described above, the composite fine particles comprising aggregates of the daughter particles and the matrix particles are formed, and in order to firmly maintain the aggregated state of the composite fine particles and to have substantially no catalytic activities by the daughter particles, the surfaces of the aggregated composite fine particles is coated with the silicones. As explained above, as for the thickness of the coating layer, thickness is considered to be sufficient if the active sites on the surface of the composite fine particles are substantially coated so as not have the surface actions affect the surrounding medium of the composite fine particles.

Suitable solvents for the starting materials for the daughter particles and the starting materials for the matrix particles mentioned above may be water or organic solvents, with preference given to those which do not inhibit the production of the composite fine particles comprising the daughter particles/matrix particles composite in the starting material liquid mixture. Examples of the organic solvents include alcohols, such as methanol and ethanol, and polar solvents, such as N,N-dimethylformamide, dimethyl sulfoxide, hexamethylphosphoramide, and ethyl acetate. As long as the formation of the ultraviolet shielding composite fine particles is not adversely affected, those solvents which may be the same ones or different ones as those for the metal oxide sol solutions mentioned above ones may be used.

The concentration of the starting materials for the daughter particles in the starting material liquid mixture, which is a liquid mixture containing the starting materials for the daughter particles and the starting materials for the matrix particles is preferably in the range of from $10^{-5}$ to 10 mol/L, desirably from $10^{-4}$ to 1 mol/L. Thus is because when the concentration of the starting materials for the daughter particles is lower than $10^{-5}$ mol/L, the amount of the daughter particles in the composite fine particles is extremely small, thereby making it difficult to exhibit good optical properties of the daughter particles. On the other hand, when the concentration is higher than 10 mol/L, the dispersion of the starting materials in the liquid becomes difficult, thereby making it difficult to form composite fine particles with a uniform composition.

The concentration of the fluorine compound in the starting material liquid mixture, which is a liquid mixture containing the starting materials for the daughter particles and the starting materials for the matrix particles is preferably in the range of from $10^{-5}$ to 10 mol/L, desirably from $10^{-4}$ to 1 mol/L. This is because when the concentration of the fluorine compounds is lower than $10^{-5}$ mol/L, the amount of the fluorine compound fine particles produced is extremely small, and when the concentration is higher than 10 mol/L, the solubility limit of the fluorine compound is reached.

The concentration of the silicones in the liquid mixture containing the composite fine particles comprising aggregates of the daughter particles/matrix particles is preferably in the range of from $10^{-5}$ to 10 mol/L, desirably from $10^{-4}$ to 1 mol/L. This is because when the concentration of the silicones is lower than $10^{-5}$ mol/L, the amount of coating formed on the surfaces of the composite fine particles by the silicones is extremely small, and when the concentration is higher than 10 mol/L, the solubility limit of the concentration of the silicones is reached.

The composite fine particles, which are coated with the silicones and comprise aggregates of the daughter particles/matrix particles dispersed in the liquid mixture, have an average particle size of preferably from 0.002 to 0.5 µm, particularly desirably not greater than 0.4 µm, further desirably not greater than 0.3 µm, and the particle size distribution should preferably be kept as narrow as possible. When the average particle size exceeds 0.5 µm, the transparency and the ultraviolet shielding ability are likely to be lowered due to the scattering of the visible light caused by the particle size effect.

The ultraviolet shielding composite fine particles of the present invention can be obtained by the production method explained above, and the structure of the ultraviolet shielding composite fine particles is such that the matrix particles comprise aggregates of primary particles which are formed while the primary particles retain their shapes, each primary particle being aggregated in a close-packed state, and that the daughter particles are dispersed on the surface and in the inner portion of the matrix particles, the aggregated composites of ultrafine fine particles of the daughter particles and the matrix particles being preferably coated with a silicone. When the dispersibility of the daughter particles is poor, good optical properties of the daughter particles are not exhibited. The ultraviolet light colliding with the daughter particles which are present on the surface of the matrix particles is partially absorbed while the remaining ultraviolet light is scattered from the composite fine particles. The ultraviolet light which does not collide with the daughter particles on the surface and further enters the inner portion of the matrix particles is absorbed and scattered by the daughter particles contained in the inner portion of the matrix particles, so that the ultraviolet light is effectively shielded. Also, by having the silicone coating layer, the catalytic activities of the daughter particles and the matrix particles are substantially inhibited, so that the composite fine particles can be stably present in a given medium without causing a deterioration of the medium.

The shapes and the sizes of the matrix particles, namely the composite fine particles, of the present invention are not particularly limited, and various shapes and sizes can be used according to different cases. For instance, when used as cosmetic powders, spherical particle powders having a particle size ranging from sub-microns to several micrometers are preferably used from the viewpoints of a good skin texture and easy handling, and the plate-like particle powders having the particle size ranges given above are preferably used from the viewpoints of providing strong adherence to the skin, excellent spreading on the skin, and easy handling.

The proportion of the daughter particles dispersed in and supported by the matrix particles is not particularly limited as long as the daughter particles can be well dispersed in the matrix particles without causing an excessive aggregation of the daughter particles in the matrix particles. The amount of the daughter particles contained in the matrix particles usually ranges from 0.1 to 85% by volume, preferably from 0.1 to 50% by volume, more preferably from 0.1 to 40% by volume, particularly preferably from 0.5 to 30% by volume. In the case where the metal oxides and the fluorine compounds are contained in the matrix particles, the minimum amount of the fluorine compounds is at least 1% by weight.

5. The optical properties of the ultraviolet shielding composite fine particles of the present invention can be quantitatively evaluated by measuring their light transmittance by an ultraviolet-visible light spectrophotometer.

The preferred ultraviolet shielding ability for the composite fine particles of the present invention is determined by a light transmittance of not less than 80% at a wavelength of 800 nm, a light transmittance of not less than 20% at a wavelength of 400 nm, and a light transmittance of not more than 5% at least at one wavelength within the range from 380 nm to 300 nm, wherein the light transmittance is determined by suspending the composite fine particles in a medium having a refractive index of substantially the same level as the composite fine particles, and measuring by an ultraviolet-visible light spectroscopy using an optical cell having an optical path length of 1 mm. By having the above properties, a high transparency particularly in the visible light region as well as a high shielding ability in the ultraviolet light region can be satisfactorily achieved. Incidentally, the phrase "a medium having a refractive index of substantially the same level as the composite fine particles" means that the difference in the refractive indices between the composite fine particles and the medium is within ±0.1, preferably within ±0.05.

The ultraviolet shielding ability mentioned above can be evaluated by an ultraviolet-visible light spectroscopy specified below.

The composite fine particles of the present invention are suspended in a medium having a refractive index of substantially the same level as the composite fine particles to prepare a suspension of composite fine particles having a given concentration. In order to prepare a uniform suspension, the composite fine particles are stirred and well dispersed using, for instance, an ultrasonic disperser, etc. An optical cell having an optical path length of 1 mm is furnished and filled with the above suspension. An optical cell may be such that no absorption or no scattering of the light in the ultraviolet light region and the visible light region take place, and, for instance, a silica cell can be used therefor. The light transmittance through the optical cell is measured using an ultraviolet-visible light spectrophotometer. In this method, a similar optical cell filled only with a medium before suspending the composite fine particles is used as a control to remove background.

Also, the composite fine particles of the present invention have substantially no catalytic activities, which may be verified, for instance, by the following method. Specifically, the composite fine particles are dispersed in white vaseline in an amount of 1% by weight, and the resulting mixture is subjected to a 60-minute irradiation treatment with ultraviolet light having a central wavelength of 312 nm using an ultraviolet light source ("ENB-260C/J," manufactured by SPECTROLINE), to determine whether or not discoloration of white vaseline takes place in the resulting mixture. In the case where the white vaseline is adversely affected by the catalytic activities, a color change undergoes of from white to brown, and thus is easily verified by the above method.

Accordingly, in the present specification, the phrase "the composite fine particles having substantially no catalytic activities" refers to the composite fine particles whose catalytic activities are inhibited to such an extent that for practical purposes they show substantially no catalytic activities. For instance, when the catalytic activities are tested by the above method, the color change of the vaseline is not found.

6. Cosmetics

The cosmetics of the present invention may be prepared by optionally blending various kinds of adjuncts conventionally used for cosmetics, in addition to the above ultraviolet shielding composite fine particles and the dispersion oil agents of the ultraviolet shielding composite fine particles. Examples thereof include the following:

(1) Inorganic powders such as talc, kaolin, sericite, muscovite, phlogopite, lepidolite, biotite, synthetic golden mica, vermiculite, magnesium carbonate, calcium carbonate, diatomateous earth, magnesium silicate, calcium silicate, aluminum silicate, barium silicate, barium sulfate, strontium silicate, metallic tungustates, silica, hydroxylapatite, zeolite, boron nitride, and ceramic powders.

(2) Organic powders such as nylon powders, polyethylene powders, polystyrene powders, benzoguanamine resin powders, polytetrafluoroethylene powders, distyrenebenzene polymer powders, epoxy resin powders, acrylic resin powders, and fine crystalline cellulose.

(3) Inorganic white pigments such as titanium oxide and zinc oxide; inorganic red pigments such as iron oxide (red oxide) and iron titanate; inorganic brown pigments such as γ-iron oxide; inorganic yellow pigments such as yellow iron oxide and yellow ochre; inorganic black pigments such as black iron oxide and carbon black; inorganic violet pigments such as manganese violet and cobalt violet; inorganic green pigments such as chromium oxide, chromium hydroxide, and cobalt titanate; inorganic blue pigments such as ultramarine and Prussian blue; pearl-like pigments such as mica coated with titanium oxide, oxychlorobismuth coated with titanium oxide, oxychlorobismuth, talc coated with titanium oxide, fish scale flake, mica coated with colored titanium oxide; and metal powder pigments such as aluminum powders and copper powders.

(4) Organic pigments including Pigment Red 201, Pigment Red 202, Pigment Red 204, Pigment Red 205, Pigment Red 220, Pigment Red 226, Pigment Red 228, Pigment Red 405, Pigment Orange 203, Pigment Orange 204, Pigment Yellow 205, Pigment Yellow 401, and Pigment Blue 404; organic pigments including zirconium lakes, barium lakes, and aluminum lakes of Pigment Red 3, Pigment Red 104, Pigment Red 106, Pigment Red 227, Pigment Red 230-(1), Pigment Red 230-(2), Pigment Red 401, Pigment Red 505, Pigment Orange 205, Pigment Yellow 4, Pigment Yellow 5, Pigment Yellow 202-(1), Pigment Yellow 202-(2), Pigment Yellow 203, Pigment Green 3, and Pigment Blue 1.

(5) Natural pigments such as chlorophyll and β-carotene.

(6) Various hydrocarbons, higher fatty acids, fats and oils, esters, higher alcohols, and waxes, such as squalane, paraffin wax, liquid paraffin, Vaseline™, microcrystalline wax, ozocerite, ceresine, myristic acid, palmitic acid, stearic acid, oleic acid, isostearic acid, cetyl alcohol, hexadecyl alcohol, oleyl alcohol, cetyl 2-ethylhexanoate, 2-ethylhexyl palmitate, 2-octyldodecyl myristate, neopentyl glycol di-2-ethylhexanoate, glycerol tri-2-ethylhexanoate, 2-octyldodecyl oleate, isopropyl myristate, glycerol triisostearate, coconut fatty acid triglyceride, olive oil, avocado oil, camellia oil, jojoba oil, beeswax, spermaceti, carnauba wax, myristyl myristate, mink oil, and lanoline; silicone oils such as volatile silicone oils and non-volatile silicone oils.

(7) The following ultraviolet protecting agents such as ultraviolet light absorbents may be optionally added in suitable amounts.

1) Benzoic acid derivatives:

p-Aminobenzoic acid (PABA), glycerol mono-p-aminobenzoate, ethyl p-N,N-dipropoxyaminobenzoate, ethyl p-N,N-diethoxyaminobenzoate, ethyl p-N,N-dimethylaminobenzoate, butyl p-N,N-dimethylaminobenzoate, amyl p-N,N-dimethylaminobenzoate, and octyl p-N,N-dimethylaminobenzoate.

2) Anthranilic acid derivatives:

Homomenthyl N-acetylanthranilate.

3) Salicylic acid derivatives:

Amyl salicylate, menthyl salicylate, homomenthyl salicylate, octyl salicylate, phenyl salicylate, benzyl salicylate, and p-isopropanolphenyl salicylate.

4) Cinnamic acid derivatives:

Octylcinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, and glycerol mono-2-ethylhexanoyl-diparamethoxycinnamate.

5) Benzophenone derivatives:

2,4-Dihydroxybenzophenone, 2,2'-dihydroxy 4-methoxybenzophenone, 2,2'-dihydroxy 4,4'-dimethoxybenzophenone, 2,2',4,4'-tetrahydroxy benzophenone, 2-hydroxy 4-methoxybenzophenone, 2-hydroxy 4-methoxy-4'-methylbenzophenone, 2-hydroxy 4-methoxybenzophenon-5-sulfonate, 4-phenylbenzophenone, 2-ethylhexyl 4'-phenylbenzophenone-2-carboxylate, 2-hydroxy 4-n-octoxybenzophenone, and 4-hydroxy 3-carboxybenzophenone.

6) Other ultraviolet absorbents:

3-(4'-Methylbenzylidene) d,l-camphor, 3-benzylidene d,l-camphor, urocanic acid, ethyl urocanate, 2-phenyl 5-methylbenzoxazole, 2,2'-hydroxy 5-methylphenylbenzotriazole, 2-(2'-hydroxy-5' t-octylphenyl)benzotriazole, dibenzarsine, dianisoylmethane, 4-methoxy 4'-t-butyldibenzoylmethane, 5-(3,3'-dimethyl-2-norbornylidene)-3-pentane-2-one, and 1-(3,4-dimethoxyphenyl)-4,4'-dimethyl-1,3-pentadione.

(8) Also, surfactants may be optionally used in suitable amounts.

Examples of the surfactants include polyoxyethylene alkyl ethers, polyoxyethylene fatty acid esters, polyoxyethylene sorbitan fatty acid esters, polyoxyethylene sorbitol fatty acid esters, alkyl polyoxyethylene hardened castor oil sulfates, alkyl polyoxyethylene sulfates, alkyl phosphates, alkyl polyoxyethylene phosphates, alkali metal salts of fatty acids, sorbitan fatty acid esters, glycerol fatty acid esters, and silicone-based surfactants, such as polyether-modified silicones.

(9) Further, water-soluble polyhydric alcohols may be optionally used in suitable amounts. Examples of the water-soluble polyhydric alcohols are water-soluble polyhydric alcohols having two or more hydroxyl groups in a molecule, including ethylene glycol, propylene glycol, 1,3-butylene glycol, 1,4-butylene glycol, dipropylene glycol, glycerol, polyglycerols, such as diglycerol, triglycerol, and tetraglycerol, glucose, maltose, maltitol, sucrose, fructose, xylitol, sorbitol, maltotriose, threitol, erythritol, and sugar alcohol derived from decomposed starch.

(10) In addition, other cosmetic adjuncts may be optionally added in suitable amounts, including amino acids, such as lysine and arginine; organic acids, such as lactic acid, citric acid, succinic acid, and glycolic acid, and organic salts thereof; resins, such as alkyd resins and urea resins; plasticizers, such as camphor and tributyl citrate; antioxidants, such as α-tocopherol; antiseptics, such as butyl p-hydroxybenzoate and methyl p-hydroxybenzoate; extracts from plants, such as cornflower, althea, and *Hypericuor erectum*; medicinal ingredients such as retinol and allantoin; binders such as xanthan gum and carrageenan; and perfumes.

Although an amount of the ultraviolet shielding composite fine particles of the present invention in cosmetics depends upon the kinds of cosmetics produced, the amount is preferably 0.01 to 50% by weight, more preferably 0.05 to 40% by weight, particularly 0.1 to 30% by weight. When the amount of the ultraviolet shielding composite fine particles is less than the lower limit thereof, sufficient shielding effects against the ultraviolet light cannot be achieved, and when the amount exceeds the upper limit thereof, a pleasant skin texture when used as cosmetics are undesirably lost. The amount of the ultraviolet shielding composite fine particles when using a dispersion oil agent composition thereof for cosmetics is determined so as to satisfy the amount specified in the cosmetics contained in the dispersion oil agent, the cosmetics comprising the ultraviolet shielding composite fine particles mentioned above.

The cosmetics of the present invention may be formulated in various forms by conventional method. Although the forms are not particularly limited, the cosmetics may be formulated as various make-up products including lotions, emulsions, creams, ointments, aerosol cosmetics, powdery foundations, powdery eyeshadows, emulsified foundation creams, and lipsticks, hair care preparations, and skin cleaners.

In addition, the cosmetics of the present invention preferably have SPF of not less than 8 and changes in color before and after skin application, determined as ΔE measured by color-and-color difference meter of not more than 3. From the viewpoint of sufficiently exhibiting the ultraviolet shielding effects, SPF is preferably not less than 8, more preferably not less than 10, particularly not less than 13. From the viewpoint of maintaining good appearance upon skin application, $\Delta E^*_{ab}$ is preferably not more than 3, more preferably not more than 2, particularly not more than 1. In the present invention, SPF is measured by using an analyzer "SPF-290" (manufactured by The Optometrics Group), and $\Delta E^*_{ab}$ is a value defined in JIS Z8729-1980.

The present invention will be described in further detail by means of the working examples of the present invention given hereinbelow, but the present invention is not limited by these examples.

EXAMPLE 1

The amount 268.3 g of a silica sol ("ST-C," manufactured by Nissan Chemical Industries, Ltd.; $SiO_2$ concentration: 20.5% by weight), 50 g of titanium oxide ultrafine particles ("MT-500SA," manufactured by TAYCA CORPORATION; rutile-type), and water were blended together to make up a volume of one liter, yielding a starting material liquid mixture. (Specifically, the concentrations of $SiO_2$ and $TiO_2$ in the starting material liquid mixture were 0.92 mol/liter and 0.63 mol/liter, respectively, and the amount of the particle mixture contained in the above starting material liquid mixture was about 10.5% by weight.)

The above starting material liquid mixture thus prepared was subjected to a pretreatment using a homogenizer ("T.K.-ROBOMICS," manufactured by Tokushu Kika Kogyo Co., Ltd.) at 12000 r.p.m. for 90 minutes. Thereafter, while agitating at 7000 r.p.m., the pretreated starting material liquid mixture was further subjected to a 8-minute dispersion treatment for 3 times using a dynomill ("KDL-PILOT," manufactured by Willy A. Bachofen AG) under the conditions of an agitation speed of 3600 r.p.m. and a solution/media ratio of 600 cc/1200 cc, to form a liquid dispersion of the $TiO_2/SiO_2$ composite fine particles.

190.5 g of the above liquid dispersion was subjected to a topping treatment using a rotary evaporator to remove water, to thereby produce a liquid dispersion which was concentrated for about three times. Thereafter, while agitating with a homogenizer, the liquid dispersion was added dropwise to and dispersed in 2000 g of ethanol.

While agitating the liquid dispersion obtained above using the homogenizer, a coating treatment for the $TiO_2$/$SiO_2$ composite fine particles was carried out by adding dropwise a mixed solution comprising 3.0 g of an oxazoline-modified silicone ("OS96-20," manufactured by Kao Corporation) dissolved in 900.0 g of ethanol and blending the mixed components.

The liquid dispersion thus obtained was further subjected to a topping treatment at 75° C. using a rotary evaporator to remove ethanol and water, to thereby concentrate the liquid dispersion for about five times.

While agitating the resulting liquid dispersion, 400.0 g of a silicone oil ("SH244," manufactured by Toray-Dow Corning Corporation; refractive index: 1.39) was added dropwise, and mixed with the liquid dispersion. Thereafter, the resulting liquid dispersion was subjected to a topping treatment at 80° C. using a rotary evaporator to remove ethanol and water.

The resulting liquid dispersion was subjected to a dispersion treatment using the homogenizer at 9000 r.p.m for 15 minutes. Thereafter, the resulting mixture was subjected to a topping treatment at 80° C. using a rotary evaporator to remove ethanol, water, and a silicone oil, so that the composite fine particles were phase-transferred and dispersed in the silicone oil, to give a silicone oil dispersion of the composite fine particles (composite fine particles: 10% by weight).

The particle size of the composite fine particles after the coating treatment was measured by subjecting the liquid dispersion comprising the $TiO_2$/$SiO_2$ composite fine particles to measurement using a laser-doppler type particle size analyzer ("DLS-700," manufactured by OTSUKA ELECTRONICS CO., LTD.). It was found that the average particle size, (volume basis), was about 0.3 µm.

A cross section of the composite fine particles after the coating treatment was observed by a transmission electron microscope using an ultrathin sectioning method. Consequently, it was found that $TiO_2$ ultrafine particles (average particle size: 0.03 µm) and $SiO_2$ ultrafine particles (average particle size: 0.01 µm) were uniformly dispersed in and supported thereby. In other words, the $TiO_2$/$SiO_2$ composite fine particles were constituted by $TiO_2$ (a band gap energy is about 3.3 eV, and a refractive index is about 2.71) and $SiO_2$ (a band gap energy is about 6.2 eV, and a refractive index is about 1.46).

The amount of the each of the particles in the above composite fine particles (subtracting the silicone coating), which was calculated based on the compositional ratio of particles in the starting material liquid, wherein particle densities of $TiO_2$ and $SiO_2$ were, respectively, 3.84 g/cm$^3$ and 2.27 g/cm$^3$ were 35.0% by volume and 65.0% by volume, respectively. The refractive index of the above composite fine particles was about 1.90, the refractive index being calculated from the volume ratio of each of the particles in the composite fine particles.

The composite fine particles after the coating treatment were dispersed in white vaseline (manufactured by Wako Pure Chemical Industries, Ltd.), so as to have a concentration of $TiO_2$ of 1% by weight in a mixture comprising the white vaseline and the composite fine particles. The resulting mixture was subjected to a 60-minute irradiation treatment with ultraviolet light having a central wavelength of 312 nm using an ultraviolet light source ("ENB-260C/J," manufactured by SPECTROLINE). The above showed that no color change took place in the white vaseline, and that the catalytic activities were substantially inhibited in the resulting composite fine particles. Incidentally, the composite fine particles after the coating treatment were treated using a dry-type pulverizing mill ("A10," manufactured by IKA-Labourtechnik), and a test was carried out in the same manner as above. As a result, no color change of the white vaseline was observed. The above showed that the catalytic activities of the milled composite fine particles were substantially inhibited in the resulting composite fine particles.

After 0.1 g of the silicone oil dispersion of the composite fine particles obtained above was diluted with and dispersed in 9.9 g of the silicone oil, the light transmittance of the resulting liquid dispersion was measured by an ultraviolet-visible light spectrophotometer ("UV-160A," manufactured by Shimadzu Corporation) using a cell having an optical path length of 1 mm. The results are shown in FIG. 1.

In the figure, the light transmittance of the composite fine particles was substantially 5% or less in the ultraviolet region B and the ultraviolet region C, the wavelengths of which were not longer than 320 nm. On the other hand, the composite fine particles show high light transmittance values in the entire visible light region at a wavelength of from 400 to 800 nm, the light transmittance at 400 nm being 40%, and at 800 nm being 84%. Accordingly, the composite fine particles thus produced had a high transparency in the visible light region and a high shielding ability in the ultraviolet region.

EXAMPLE 2

The formation of the composite fine particles of $TiO_2$/$SiO_2$, the concentration of the liquid dispersion, and the dispersion of the concentrated liquid dispersion to ethanol were carried out in the same manner as in Example 1.

The formed liquid dispersion was further subjected to a topping treatment at 75° C. using a rotary evaporator to remove ethanol and water, to thereby produce a liquid dispersion which was concentrated for about five times. Thereafter, 1600 g of isopropyl alcohol was added dropwise to the concentrated liquid dispersion while agitating using a homogenizer.

While the resulting liquid dispersion was agitated using a homogenizer, the composite fine particles of $TiO_2$/$SiO_2$ were subjected to coating treatment by adding dropwise a liquid mixture previously prepared by dissolving 3.0 g of an amino-modified silicone ("XF42-B0819," manufactured by Toshiba Silicone Corporation; molecular weight: 10000; and amino equivalency: 1600) in 900.0 g of isopropyl alcohol to the liquid dispersion and blending the resulting liquid mixture.

The resulting liquid dispersion was subjected to a topping treatment at 80° C. using a rotary evaporator to remove ethanol, isopropyl alcohol, and water, to thereby produce a liquid dispersion which was concentrated for about five times.

While the resulting liquid dispersion was agitated, 400.0 g of the silicone oil (the same one as in Example 1) was added dropwise and mixed with the liquid dispersion. Thereafter, the resulting mixture was subjected to a topping treatment at 80° C. using a rotary evaporator to remove ethanol, isopropyl alcohol, and water.

The resulting liquid dispersion was subjected to a dispersion treatment using the homogenizer at 9000 r.p.m for 15 minutes. Thereafter, the resulting mixture was subjected to a topping treatment at 80° C. using a rotary evaporator to remove ethanol, water, and a silicone oil, so that the composite fine particles were phase-transferred and dispersed in the silicone oil, to give a silicone oil dispersion of the composite fine particles (composite fine particles: 20% by weight).

The particle size of the composite fine particles after the coating treatment was measured by subjecting the liquid dispersion comprising the $TiO_2/SiO_2$ composite fine particles to measurement using a laser-doppler type particle size analyzer ("DLS-700," manufactured by OTSUKA ELECTRONICS CO., LTD.). It was found that the average particle size, (volume basis), was about 0.3 $\mu$m.

A cross section of the composite fine particles after the coating treatment was observed by a transmission electron microscope using an ultrathin sectioning method. Consequently, it was found that $TiO_2$ ultrafine particles (average particle size: 0.03 $\mu$m) and $SiO_2$ ultrafine particles (average particle size: 0.01 $\mu$m) were uniformly dispersed in and supported thereby. In other words, the $TiO_2/SiO_2$ composite fine particles were constituted by $TiO_2$ (a band gap energy is about 3.3 eV, and a refractive index is about 2.71) and $SiO_2$ (a band gap energy is about 6.2 eV, and a refractive index is about 1.46).

The amount of the each of the particles in the above composite fine particles (subtracting the silicone coating), which was calculated based on the compositional ratio of particles in the starting material liquid, wherein particle densities of $TiO_2$ and $SiO_2$ were, respectively, 3.84 g/cm$^3$ and 2.27 g/cm$^3$ were 35.0% by volume and 65.0% by volume, respectively. The refractive index of the above composite fine particles was about 1.90, the refractive index being calculated from the volume ratio of each of the particles in the composite fine particles.

The composite fine particles after the coating treatment were dispersed in white vaseline (the same one as Example 1), so as to have a concentration of $TiO_2$ of 1% by weight in a mixture comprising the white vaseline and the composite fine particles. The resulting mixture was subjected to a test similar to that of Example 1. The above showed that no color change took place in the white vaseline, and that the catalytic activities were substantially inhibited in the resulting composite fine particles.

Figure 2:
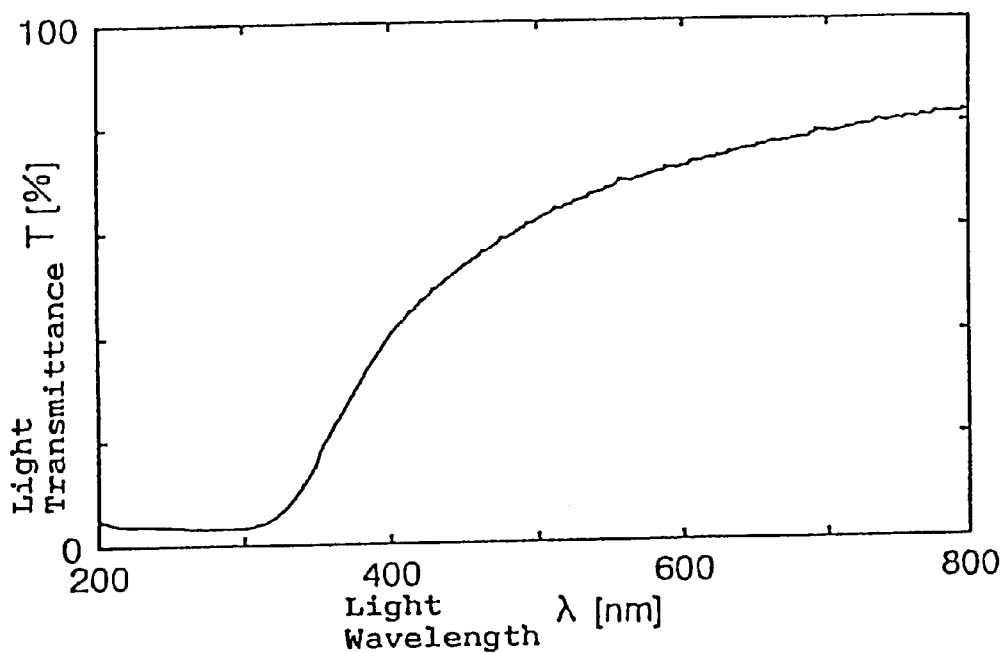
FIG. 2 is a chart showing the measurement results of the light transmittance of the ultraviolet shielding composite fine particles obtained in Example 2, as measured by an ultraviolet-visible light spectrophotometer.

After 0.05 g of the silicone oil dispersion of the composite fine particles obtained above was diluted with and dispersed in 9.95 g of the silicone oil, the light transmittance of the resulting liquid dispersion was measured by a method similar to that of Example 1. The results are shown in FIG. 2.

In the figure, the light transmittance of the composite fine particles was substantially 5% or less in the ultraviolet region B and the ultraviolet region C, the wavelengths of which were not longer than 320 nm. On the other hand, the composite fine particles show high light transmittance values in the entire visible light region at a wavelength of from 400 to 800 nm, the light transmittance at 400 nm being 41%, and at 800 nm being 82%. Accordingly, the composite fine particles thus produced had a high transparency in the visible light region and a high shielding ability in the ultraviolet region.

EXAMPLE 3

The amount 268.3 g of a silica sol ("ST-C," manufactured by Nissan Chemical Industries, Ltd.; $SiO_2$ concentration: 20.5% by weight), 50.0 g of titanium oxide ultrafine particles ("MT-600SA," manufactured by TAYCA CORPORATION; rutile-type), and water were blended together to make up a volume of one liter, yielding a starting material liquid mixture. (Specifically, the concentrations of $SiO_2$ and $TiO_2$ in the starting material liquid mixture were 0.92 mol/liter and 0.63 mol/liter, respectively, and the amount of the particle mixture contained in the above starting material liquid mixture was about 10.5% by weight.)

This starting material liquid mixture was subjected to a dispersion treatment in the same manner as in Example 1, to give a liquid dispersion of the $TiO_2/SiO_2$ composite fine particles. Thereafter, in the same manner as in Example 1, the liquid dispersion was concentrated and then the concentrated liquid dispersion was dispersed in ethanol.

While agitating the liquid dispersion obtained above using the homogenizer, a coating treatment for the $TiO_2/SiO_2$ composite fine particles was carried out by adding dropwise a mixed solution comprising 3.0 g of an oxazoline-modified silicone ("OS96-20," manufactured by Kao Corporation) dissolved in 900.0 g of ethanol and blending the mixed components.

The liquid dispersion thus obtained was further subjected to a topping treatment at 75° C. using a rotary evaporator to remove ethanol and water, to thereby concentrate the liquid dispersion for about five times.

While agitating the resulting liquid dispersion, 400.0 g of a silicone oil (the same one as in Example 1) was added dropwise, and mixed with the liquid dispersion. Thereafter, the resulting liquid dispersion was subjected to a topping treatment at 80° C. using a rotary evaporator to remove ethanol, isopropyl alcohol, and water.

The resulting liquid dispersion was subjected to a dispersion treatment using the homogenizer at 9000 r.p.m for 15 minutes. Thereafter, the resulting mixture was subjected to a topping treatment at 80° C. using a rotary evaporator to remove ethanol, isopropyl alcohol, water, and a silicone oil, so that the composite fine particles were phase-transferred and dispersed in the silicone oil, to give a silicone oil dispersion of the composite fine particles (composite fine particles: 20% by weight).

The resulting silicone oil dispersion of the composite fine particles was sufficiently dried at 130° C. using a kneader ("PNV-1H" manufactured by Irie Shokai K.K.), to give a composite fine particle powder.

The resulting composite fine particle powder was pulverized using a counter jet mill ("100AFG" manufactured by Hosokawa Micron Corporation), to give composite fine particles.

The particle size of the composite fine particles after the coating treatment was measured by subjecting the $TiO_2/SiO_2$ composite fine particles to measurement using a laser-doppler type particle size analyzer ("DLS-700," manufactured by OTSUKA ELECTRONICS CO., LTD.). It was found that the average particle size, (volume basis), was about 0.3 $\mu$m.

A cross section of the composite fine particles after the coating treatment was observed by a transmission electron microscope using an ultrathin sectioning method. Consequently, it was found that $TiO_2$ ultrafine particles (average particle size: 0.05 $\mu$m) and $SiO_2$ ultrafine particles (average particle size: 0.01 $\mu$m) were uniformly dispersed in and supported thereby. In other words, the $TiO_2/SiO_2$ composite fine particles were constituted by $TiO_2$ (a band gap energy is about 3.3 eV, and a refractive index is about 2.71) and $SiO_2$ (a band gap energy is about 6.2 eV, and a refractive index is about 1.46).

The amount of the each of the particles in the above composite fine particles (subtracting the silicone coating), which was calculated based on the compositional ratio of particles in the starting material liquid, wherein particle densities of $TiO_2$ and $SiO_2$ were, respectively, 3.84 g/cm$^3$ and 2.27 g/cm$^3$ were 35.0% by volume and 65.0% by volume, respectively. The refractive index of the above composite fine particles was about 1.90, the refractive index being calculated from the volume ratio of each of the particles in the composite fine particles.

The composite fine particles after the coating treatment were dispersed in white vaseline (the same one as in Example 1), so as to have a concentration of $TiO_2$ of 1% by weight in a mixture comprising the white vaseline and the composite fine particles. The resulting mixture was subjected to a test similar to that of Example 1. The above showed that no color change took place in the white vaseline, and that the catalytic activities were substantially inhibited in the resulting composite fine particles.

Figure 3:
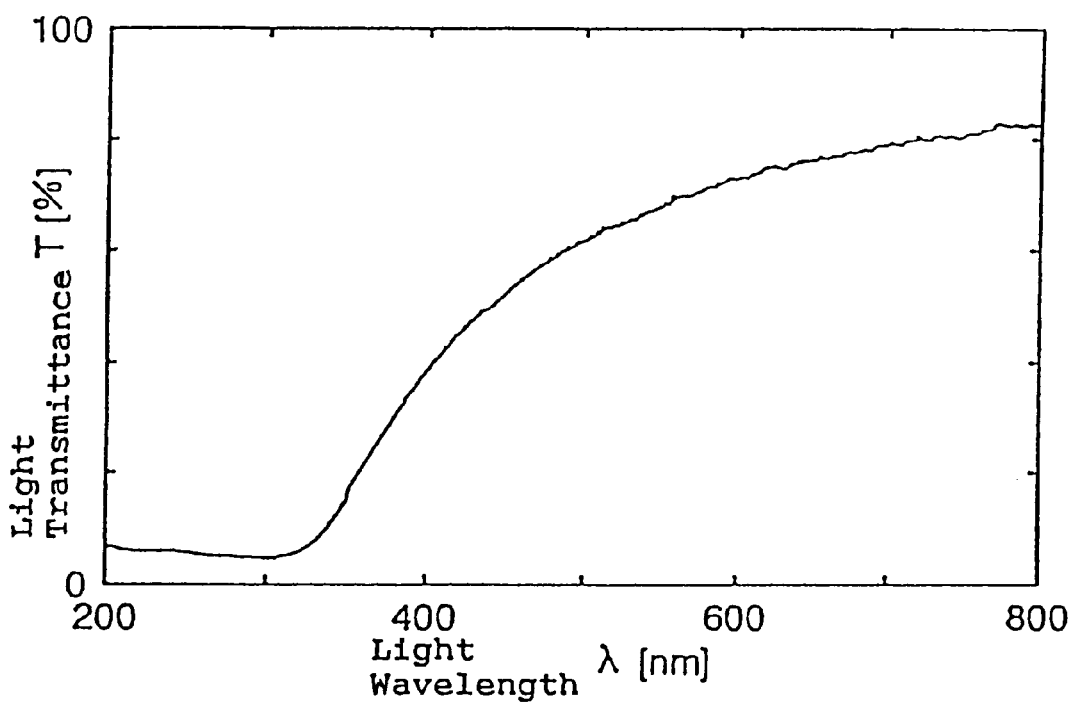
FIG. 3 is a chart showing the measurement results of the light transmittance of the ultraviolet shielding composite fine particles obtained in Example 3, as measured by an ultraviolet-visible light spectrophotometer.

After 0.01 g of the silicone oil dispersion of the composite fine particles obtained above was diluted with and dispersed in 9.99 g of the silicone oil, the light transmittance of the resulting liquid dispersion was measured by a method similar to that of Example 1. The results are shown in FIG. 3.

In the figure, the light transmittance of the composite fine particles was substantially 5% or less in the ultraviolet region B and the ultraviolet region C, the wavelengths of which were not longer than 305 nm. On the other hand, the composite fine particles show high light transmittance values in the entire visible light region at a wavelength of from 400 to 800 nm, the light transmittance at 400 nm being 39%, and at 800 nm being 83%. Accordingly, the composite fine particles thus produced had a high transparency in the visible light region and a high shielding ability in the ultraviolet region.

EXAMPLE 4

The amount 61.0 g of a silica sol ("ST-C," manufactured by Nissan Chemical Industries, Ltd.; $SiO_2$ concentration: 20.5% by weight), 87.5 g of zinc oxide ultrafine particles (fine zinc flower, manufactured by Sakai Kagaku K.K.), and water were blended together to make up a volume of one liter, yielding a starting material liquid mixture. (Specifically, the concentrations of $SiO_2$ and ZnO in the starting material liquid mixture were 0.21 mol/liter and 1.08 mol/liter, respectively, and the amount of the particle mixture contained in the above starting material liquid mixture was about 10% by weight.)

The starting material liquid mixture was subjected to a dispersion treatment in the same manner as in Example 1, to give a liquid dispersion of the ZnO/$SiO_2$ composite fine particles.

The amount 200 g of the above liquid dispersion was subjected to a topping treatment using a rotary evaporator to remove water, to thereby produce a liquid dispersion which was concentrated for about three times. Thereafter, while agitating with a homogenizer, the liquid dispersion was added dropwise to and dispersed in 2000 g of ethanol. Further, the liquid dispersion was subjected to a dispersion treatment using an ultrasonic disperser for 60 minutes.

While agitating the liquid dispersion obtained above using the homogenizer, a coating treatment for the ZnO/$SiO_2$ composite fine particles was carried out by adding dropwise a mixed solution comprising 3.0 g of an oxazoline-modified silicone ("OS96-20," manufactured by Kao Corporation) dissolved in 900.0 g of ethanol and blending the mixed components.

The liquid dispersion thus obtained was further subjected to a topping treatment at 75° C. using a rotary evaporator to remove ethanol and water, to thereby concentrate the liquid dispersion for about five times.

While agitating the resulting liquid dispersion, 400.0 g of a silicone oil ("SH244," manufactured by Toray-Dow Corning Corporation; refractive index: 1.39) was added dropwise, and mixed with the liquid dispersion. Thereafter, the resulting liquid dispersion was subjected to a topping treatment at 80° C. using a rotary evaporator to remove ethanol and water.

The resulting liquid dispersion was subjected to a dispersion treatment using the homogenizer at 9000 r.p.m for 15 minutes. Thereafter, the resulting mixture was subjected to a topping treatment at 80° C. using a rotary evaporator to remove ethanol, water, and a silicone oil, so that the composite fine particles were phase-transferred and dispersed in the silicone oil, to give a silicone oil dispersion of the composite fine particles (composite fine particles: 10% by weight).

The particle size of the composite fine particles after the coating treatment was measured by subjecting the liquid dispersion comprising the ZnO/$SiO_2$ composite fine particles to measurement using a laser-doppler type particle size analyzer ("DLS-700," manufactured by OTSUKA ELECTRONICS CO., LTD.). It was found that the average particle size, (volume basis), was about 0.3 μm.

A cross section of the composite fine particles after the coating treatment was observed by a transmission electron microscope using an ultrathin sectioning method. Consequently, it was found that ZnO fine particles (average particle size: about 0.1 μm) and $SiO_2$ ultrafine particles (average particle size: 0.01 μm) were uniformly dispersed in and supported thereby. In other words, the ZnO/$SiO_2$ composite fine particles were constituted by ZnO (a band gap energy is about 3.2 eV, and a refractive index is about 1.99) and $SiO_2$ (a band gap energy is about 6.2 eV, and a refractive index is about 1.46).

The amount of the each of the particles in the above composite fine particles (subtracting the silicone coating), which was calculated based on the compositional ratio of particles in the starting material liquid, wherein particle densities of ZnO and $SiO_2$ were, respectively, 5.78 g/cm$^3$ and 2.27 g/cm$^3$ were 73.3% by volume and 26.7% by volume, respectively. The refractive index of the above composite fine particles was about 1.85, the refractive index being calculated from the volume ratio of each of the particles in the composite fine particles.

The composite fine particles after the coating treatment were dispersed in white vaseline (same one as in Example 1), so as to have a concentration of ZnO of 1% by weight in a mixture comprising the white vaseline and the composite fine particles. The resulting mixture was subjected to a test similar to that of Example 1. The above showed that no color change took place in the white vaseline, and that the catalytic activities were substantially inhibited in the resulting composite fine particles.

Figure 4:
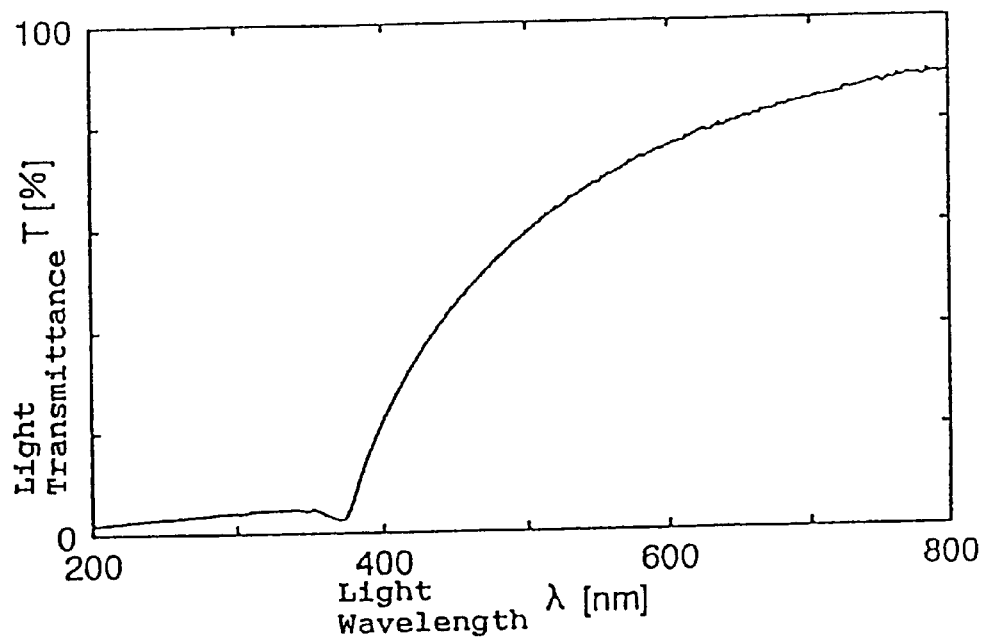
FIG. 4 is a chart showing the measurement results of the light transmittance of the ultraviolet shielding composite fine particles obtained in Example 4, as measured by an ultraviolet-visible light spectrophotometer.

After 0.14 g of the silicone oil dispersion of the composite fine particles obtained above was diluted with and dispersed in 9.86 g of the silicone oil, the light transmittance of the resulting liquid dispersion was measured by a method similar to that of Example 1. The results are shown in FIG. 4.

In the figure, the light transmittance of the composite fine particles was substantially 5% or less in the ultraviolet region B and the ultraviolet region C, the wavelengths of which were not longer than 320 nm. On the other hand, the composite fine particles show high light transmittance values in the entire visible light region at a wavelength of from 400 to 800 nm, the light transmittance at 400 nm being 22%, and at 800 nm being 89%. Accordingly, the composite fine particles thus produced had a high transparency in the visible light region and a high shielding ability in the ultraviolet region.

EXAMPLE 5

The amount 61.0 g of a silica sol ("ST-C," manufactured by Nissan Chemical Industries, Ltd.; $SiO_2$ concentration: 20.5% by weight), 12.5 g of titanium oxide ultrafine particles ("TTO-51(A)," manufactured by Ishihara Sangyo Kaisha, Ltd.; rutile-type), 75.0 g of zinc oxide fine particles (fine zinc flower, manufactured by Sakai Kagaku K.K.), and water were blended together to make up a volume of one liter, yielding a starting material liquid mixture. (Specifically, the concentrations of $SiO_2$ and $TiO_2$ in the starting material liquid mixture were 0.21 mol/liter, 0.16 mol/liter, and 0.92 mol/liter, respectively, and the amount of the particle mixture contained in the above starting material liquid mixture was about 10% by weight.)

The starting material liquid mixture was subjected to a dispersion treatment in the same manner as in Example 1, to give a liquid dispersion of the $TiO_2/ZnO/SiO_2$ composite fine particles.

The amount 200 g of the above liquid dispersion was subjected to a topping treatment using a rotary evaporator to remove water, to thereby produce a liquid dispersion which was concentrated for about three times. Thereafter, while agitating with a homogenizer, the liquid dispersion was added dropwise to and dispersed in 2000 g of ethanol. Further, the liquid dispersion was subjected to a dispersion treatment using an ultrasonic disperser for 60 minutes.

While agitating the liquid dispersion obtained above using the homogenizer, a coating treatment for the $TiO_2/ZnO/SiO_2$ composite fine particles was carried out by adding dropwise a mixed solution comprising 3.0 g of an oxazoline-modified silicone ("OS96-20," manufactured by Kao Corporation) dissolved in 900.0 g of ethanol and blending the mixed components.

The liquid dispersion thus obtained was further subjected to a topping treatment at 75° C. using a rotary evaporator to remove ethanol and water, to thereby concentrate the liquid dispersion for about five times.

While agitating the resulting liquid dispersion, 400.0 g of a silicone oil ("SH244," manufactured by Toray-Dow Corning Corporation; refractive index: 1.39) was added dropwise, and mixed with the liquid dispersion. Thereafter, the resulting liquid dispersion was subjected to a topping treatment at 80° C. using a rotary evaporator to remove ethanol and water.

The resulting liquid dispersion was subjected to a dispersion treatment using the homogenizer at 9000 r.p.m for 15 minutes. Thereafter, the resulting mixture was subjected to a topping treatment at 80° C. using a rotary evaporator to remove ethanol, water, and a silicone oil, so that the composite fine particles were phase-transferred and dispersed in the silicone oil, to give a silicone oil dispersion of the composite fine particles (composite fine particles: 25% by weight).

The particle size of the composite fine particles after the coating treatment was measured by subjecting the liquid dispersion comprising the $TiO_2/ZnO/SiO_2$ composite fine particles to measurement using a laser-doppler type particle size analyzer ("DLS-700," manufactured by OTSUKA ELECTRONICS CO., LTD.). It was found that the average particle size, (volume basis), was about 0.2 μm.

A cross section of the composite fine particles after the coating treatment was observed by a transmission electron microscope using an ultrathin sectioning method. Consequently, it was found that $TiO_2$ ultrafine particles (average particle size: 0.01 μm), ZnO fine particles (average particle size: about 0.1 μm), and $SiO_2$ ultrafine particles (average particle size: 0.01 μm) were uniformly dispersed in and supported thereby. In other words, the $TiO_2/ZnO/SiO_2$ composite fine particles were constituted by $TiO_2$ (a band gap energy is about 3.3 eV, and a refractive index is about 2.71), ZnO (a band gap energy is about 3.2 eV, and a refractive index is about 1.99), and $SiO_2$ (a band gap energy is about 6.2 eV, and a refractive index is about 1.46).

The amount of the each of the particles in the above composite fine particles (subtracting the silicone coating), which was calculated based on the compositional ratio of particles in the starting material liquid, wherein particle densities of $TiO_2$, ZnO, and $SiO_2$ were, respectively, 3.84 g/cm$^3$, 5.78 g/cm$^3$, and 2.27 g/cm$^3$ were 15.0% by volume, 59.7% by volume, and 25.3% by volume, respectively. The refractive index of the above composite fine particles was about 1.96, the refractive index being calculated from the volume ratio of each of the particles in the composite fine particles.

The composite fine particles after the coating treatment were dispersed in white vaseline (same one as in Example 1), so as to have a total concentration of $TiO_2$ and ZnO of 1% by weight in a mixture comprising the white vaseline and the composite fine particles. The resulting mixture was subjected to a test similar to that of Example 1. The above showed that no color change took place in the white vaseline, and that the catalytic activities were substantially inhibited in the resulting composite fine particles.

Figure 5:
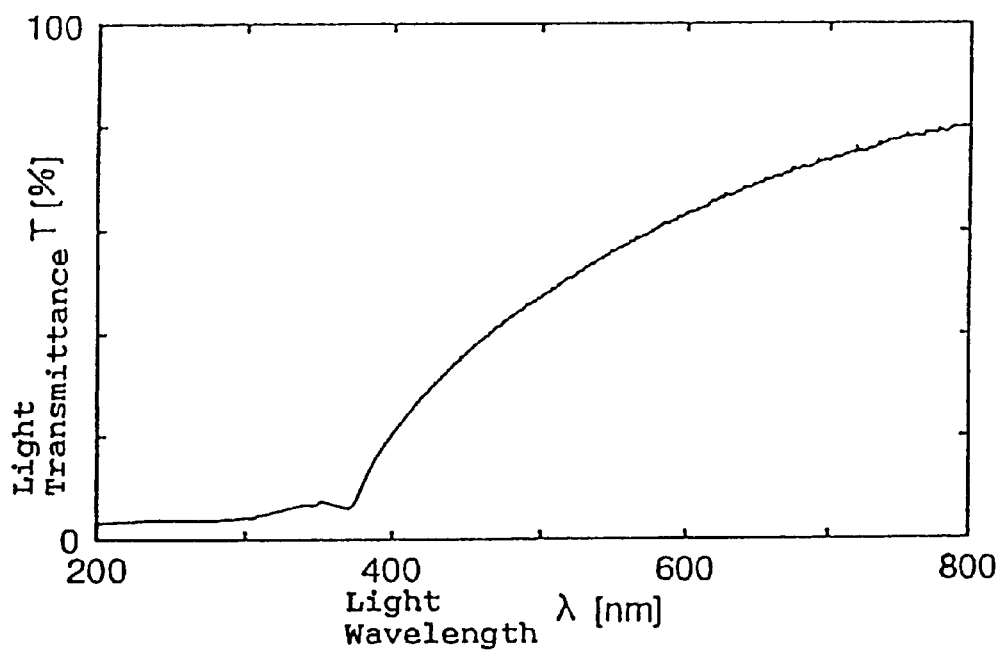
FIG. 5 is a chart showing the measurement results of the light transmittance of the ultraviolet shielding composite fine particles obtained in Example 5, as measured by an ultraviolet-visible light spectrophotometer.

After 0.056 g of the silicone oil dispersion of the composite fine particles obtained above was diluted with and dispersed in 9.944 g of the silicone oil, the light transmittance of the resulting liquid dispersion was measured by a method similar to that of Example 1. The results are shown in FIG. 5.

In the figure, the light transmittance of the composite fine particles was substantially 5% or less in the ultraviolet region B and the ultraviolet region C, the wavelengths of which were not longer than 315 nm. On the other hand, the composite fine particles show high light transmittance values in the entire visible light region at a wavelength of from 400 to 800 nm, the light transmittance at 400 nm being 21%, and at 800 nm being 80%. Accordingly, the composite fine particles thus produced had a high transparency in the visible light region and a high shielding ability in the ultraviolet region.

EXAMPLE 6

The amount 61.0 g of a silica sol ("ST-C," manufactured by Nissan Chemical Industries, Ltd.; $SiO_2$ concentration: 20.5% by weight), 12.5 g of titanium oxide ultrafine particles ("TTO-51(A)," manufactured by Ishihara Sangyo Kaisha, Ltd.; rutile-type), 75.0 g of zinc oxide fine particles ("FZN," manufactured by Kao Corporation), and water were blended together to make up a volume of one liter, yielding a starting material liquid mixture. (Specifically, the concentrations of $SiO_2$ and $TiO_2$ in the starting material liquid mixture were 0.21 mol/liter, 0.16 mol/liter, and 0.92 mol/liter, respectively, and the amount of the particle mixture contained in the above starting material liquid mixture was about 10% by weight.) The formation of the composite fine particles of $TiO_2/ZnO/SiO_2$, the concentration of the liquid dispersion, and the dispersion of the concentrated liquid dispersion to ethanol were carried out in the same manner as in Example 5.

While agitating the liquid dispersion obtained above using the homogenizer, a coating treatment for the $TiO_2$/ZnO/$SiO_2$ composite fine particles was carried out by adding dropwise a mixed solution comprising 3.0 g of an oxazoline-modified silicone ("OS96-20," manufactured by Kao Corporation) dissolved in 900.0 g of ethanol and blending the mixed components.

The liquid dispersion thus obtained was further subjected to a topping treatment at 75° C. using a rotary evaporator to remove ethanol and water, to thereby concentrate the liquid dispersion for about five times.

While agitating the resulting liquid dispersion, 400.0 g of a silicone oil ("SH244," manufactured by Toray-Dow Corning Corporation; refractive index: 1.39) was added dropwise, and mixed with the liquid dispersion. Thereafter, the resulting liquid dispersion was subjected to a topping treatment at 80° C. using a rotary evaporator to remove ethanol and water.

The resulting liquid dispersion was subjected to a dispersion treatment using the homogenizer at 9000 r.p.m for 15 minutes. Thereafter, the resulting mixture was subjected to a topping treatment at 80° C. using a rotary evaporator to remove ethanol, water, and a silicone oil, so that the composite fine particles were phase-transferred and dispersed in the silicone oil, to give a silicone oil dispersion of the composite fine particles (composite fine particles: 25% by weight).

The particle size of the composite fine particles after the coating treatment was measured by subjecting the liquid dispersion comprising the $TiO_2$/ZnO/$SiO_2$ composite fine particles to measurement using a laser-doppler type particle size analyzer ("DLS-700," manufactured by OTSUKA ELECTRONICS CO., LTD.). It was found that the average particle size, (volume basis), was about 0.2 µm.

A cross section of the composite fine particles after the coating treatment was observed by a transmission electron microscope using an ultrathin sectioning method. Consequently, it was found that $TiO_2$ ultrafine particles (average particle size: 0.01 µm), ZnO fine particles (average particle size: about 0.1 µm), and $SiO_2$ ultrafine particles (average particle size: 0.01 µm) were uniformly dispersed in and supported thereby. In other words, the $TiO_2$/ZnO/$SiO_2$ composite fine particles were constituted by $TiO_2$ (a band gap energy is about 3.3 eV, and a refractive index is about 2.71), ZnO (a band gap energy is about 3.2 eV, and a refractive index is about 1.99), and $SiO_2$ (a band gap energy is about 6.2 eV, and a refractive index is about 1.46).

The amount of the each of the particles in the above composite fine particles (subtracting the silicone coating), which was calculated based on the compositional ratio of particles in the starting material liquid, wherein particle densities of $TiO_2$, ZnO, and $SiO_2$ were, respectively, 3.84 g/cm³, 5.78 g/cm³, and 2.27 g/cm³ were 15.0% by volume, 59.7% by volume, and 25.3% by volume, respectively. The refractive index of the above composite fine particles was about 1.96, the refractive index being calculated from the volume ratio of each of the particles in the composite fine particles.

The composite fine particles after the coating treatment were dispersed in white vaseline (same one as in Example 1), so as to have a total concentration of $TiO_2$ and ZnO of 1% by weight in a mixture comprising the white vaseline and the composite fine particles. The resulting mixture was subjected to a test similar to that of Example 1. The above showed that no color change took place in the white vaseline, and that the catalytic activities were substantially inhibited in the resulting composite fine particles.

Figure 6:
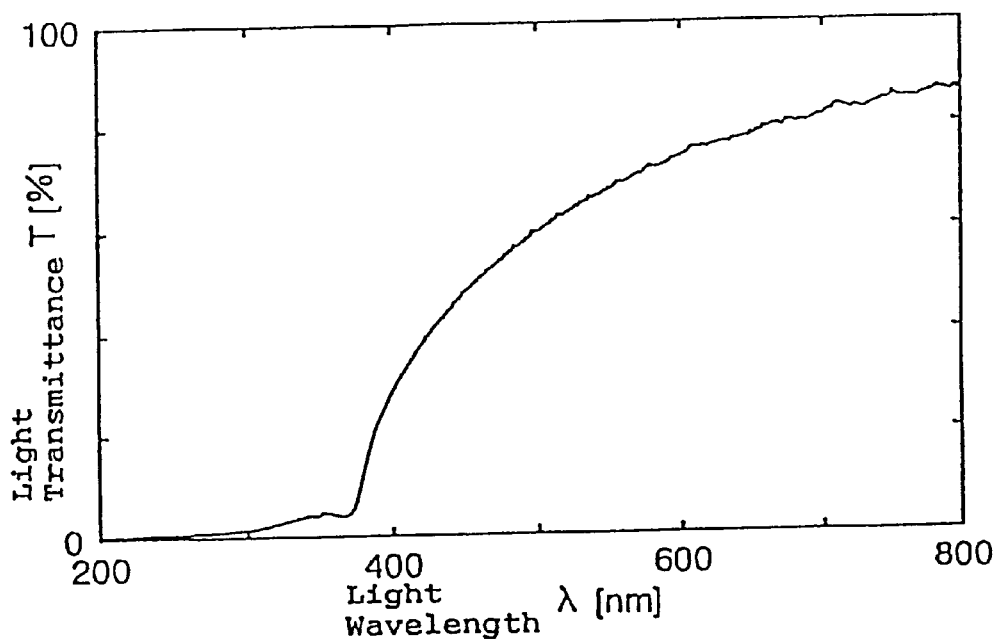
FIG. 6 is a chart showing the measurement results of the light transmittance of the ultraviolet shielding composite fine particles obtained in Example 6, as measured by an ultraviolet-visible light spectrophotometer.

After 0.056 g of the silicone oil dispersion of the composite fine particles obtained above was diluted with and dispersed in 9.944 g of the silicone oil, the light transmittance of the resulting liquid dispersion was measured by a method similar to that of Example 1. The results are shown in FIG. 6.

In the figure, the light transmittance of the composite fine particles was substantially 5% or less in the ultraviolet region B and the ultraviolet region C, the wavelengths of which were not longer than 320 nm. On the other hand, the composite fine particles show high light transmittance values in the entire visible light region at a wavelength of from 400 to 800 nm, the light transmittance at 400 nm being 28%, and at 800 nm being 86%. Accordingly, the composite fine particles thus produced had a high transparency in the visible light region and a high shielding ability in the ultraviolet region.

COMPARATIVE EXAMPLE

A starting material liquid mixture using the same starting materials and composition as in Example 6 was prepared. The resulting starting material liquid mixture was subjected to a dispersion treatment in the same manner as in Example 1, to prepare a liquid dispersion comprising the composite fine particles of $TiO_2$/ZnO/$SiO_2$. Next, the concentration of the liquid dispersion comprising the composite fine particles of $TiO_2$/ZnO/$SiO_2$ and the dispersion of the concentrated liquid dispersion to ethanol were carried out in the same manner as in Example 5.

While agitating the liquid dispersion obtained above using the homogenizer, a mixture comprising 900.0 g of ethanol in which the oxazoline-modified silicone (the same one as in Example 6) was not dissolved was added dropwise, and the ingredients were blended. Without subjecting the composite fine particles of $TiO_2$/ZnO/$SiO_2$ to a water repellent treatment, the resulting liquid mixture was further subjected to a topping treatment at 75° C. using a rotary evaporator to remove ethanol and water, to thereby concentrate the liquid dispersion for about five times.

While agitating the resulting liquid mixture, 400.0 g of a silicone oil (the same one as in Example 6) was added dropwise, and mixed with the liquid mixture. Thereafter, the resulting liquid mixture was subjected to a topping treatment at 80° C. using a rotary evaporator to remove ethanol and water.

The resulting liquid mixture was subjected to a dispersion treatment using the homogenizer at 9000 r.p.m for 15 minutes. Thereafter, the resulting mixture was subjected to a topping treatment at 80° C. using a rotary evaporator to remove ethanol, water, and a silicone oil, in order that the composite fine particles were phase-transferred and dispersed in the silicone oil. However, since the composite fine particles are not subjected to a water repellent treatment, the composite fine particles were aggregated and sedimented in the silicone oil without being dispersed therein.

The aggregated and sedimented particles were dispersed in white vaseline (same one as in Example 1), so as to have a total concentration of $TiO_2$ and ZnO of 1% by weight in a mixture comprising the white vaseline and the composite fine particles. The resulting mixture was subjected to a test similar to that of Example 1. The above showed that color of the white vaseline changed to brown, and that the catalytic activities were not inhibited in the resulting particles. This reason that the catalytic activities are not inhibited in the resulting particles is that the particles are not subjected to a water repellent treatment, namely, that no coating layers are formed by the oxazoline-modified silicone on the surface of the particles.

Industrial Applicability

The composite fine particles of the present invention, being dispersed in a liquid or solid medium, show high light transmittance in the visible light region and high shielding ability in the ultraviolet light region by exhibiting absorption and scattering ability of the daughter particles. Although the daughter particles having high catalytic activities are present in the inner portion of the composite fine particles or surfaces thereof, the surrounding medium is not substantially impaired by the catalytic activities of the daughter particles by coating the surfaces of the aggregated composites of ultrafine particles comprising daughter particles and matrix particles with a particular silicone. Moreover, coating the surfaces of the composite fine particles contributes to dispersion stability of the composite fine particles in a medium. In other words, the composite fine particles of the present invention are characterized in that, by forming composite fine particles comprising the ultrafine particles having the ultraviolet shielding ability and by coating the surfaces of the resulting composite fine particles with a particular silicone, they have substantially no catalytic activities, stably showing such optical properties of the ultrafine particles as high transparency in the visible light region and high shielding ability in the ultraviolet light region, and in a size of the level of fine particles which are easy to handle. In addition, the composite fine particles of the present invention, since they are subjected to a coating treatment with a particular silicone, are uniformly and stably dispersed even when formulated in oil-based cosmetics, so that no deterioration of cosmetic base materials takes place. When the composite fine particles are formulated in cosmetics, those cosmetics have good smoothness, excellent extensibility on skin, substantially no unevenness, excellent transparency, no unnatural skin whitening, high ultraviolet shielding effects, and high safety and stability. Further, since the composite fine particles of the present invention have excellent transparency, the color tone of the cosmetics is not affected, having a high degree of freedom in the formulation amount in cosmetics.

What is claimed is:

1. Ultraviolet shielding composite fine particles having transparency in a visible light region, comprising matrix particles comprising an aggregate of primary particles having an average particle size of from 0.001 to 0.3 $\mu$m, said aggregate being formed while the primary particles retain their shapes; and daughter particles having an average particle size of not more than 0.2 $\mu$m, said daughter particles being dispersed in and supported by said matrix particles, wherein said daughter particles have a smaller band gap energy than the particles constituting said matrix particles and are capable of absorbing ultraviolet light, and wherein the surfaces of said composite fine particles are coated with one or more silicones selected from the group consisting of modified silicones, reactive silicones, and silicone-modified copolymers, and wherein the ultraviolet shielding composite fine particles have substantially no catalytic activities.

2. The ultraviolet shielding composite fine particles according to claim 1, wherein said modified silicones are oxazoline-modified silicones or amino-modified silicones.

3. The ultraviolet shielding composite fine particles according to claim 1, wherein said particles constituting the matrix particles have a band gap energy of from 3 to 9 eV.

4. The ultraviolet shielding composite fine particles according to claim 1, wherein the band gap energy of the daughter particles is smaller than that of the particles constituting the matrix particles by not less than 0.2 eV.

5. The ultraviolet shielding composite fine particles according to claim 1, wherein said daughter particles are dispersed in and supported by said matrix particles in an amount of from 0.1 to 85% by volume.

6. The ultraviolet shielding composite fine particles according to claim 1, wherein the average particle size of the ultraviolet shielding composite fine particles is not more than 0.5 $\mu$m.

7. The ultraviolet shielding composite fine particles according to claim 1, wherein the average refractive index of the ultraviolet shielding composite fine particles is from 1.3 to 2.5.

8. The ultraviolet shielding composite fine particles according to claim 1, wherein said particles constituting the matrix particles are selected from the group consisting of metal oxides and fluorine compounds.

9. The ultraviolet shielding composite fine particles according to claim 8, wherein said metal oxide is selected from the group consisting of $SiO_2$ and $Al_2O_3$.

10. The ultraviolet shielding composite fine particles according to claim 1, wherein said daughter particles are one or more members selected from the group consisting of $TiO_2$, $ZnO$, $CeO_2$, $WO_3$, $SnO_2$, $BaTiO_3$, $CaTiO_3$, $SrTiO_3$, and $SiC$.

11. The ultraviolet shielding composite fine particles according to claim 1, wherein said ultraviolet shielding composite fine particles have a light transmittance of 80% or more at a wavelength of 800 nm, a light transmittance of 20% or more at a wavelength of 400 nm, and a light transmittance of 5% or less at a certain wavelength within the range from 380 nm to 300 nm, the light transmittance being determined by suspending said composite fine particles in a medium having substantially the same refractive index level as the composite fine particles, and measuring with an ultraviolet-visible light spectrophotometer using an optical cell having an optical path length of 1 mm.

12. The ultraviolet shielding composite fine particles according to claim 1, obtained by the steps of:

(a) preparing a liquid mixture comprising starting materials for matrix particles which are one or more materials selected form the group consisting of sols containing particles constituting matrix particles and powders of the matrix particles, the matrix particles having a primary particle with an average particle size of from 0.001 to 0.3 $\mu$m; and starting materials for daughter particles which are one or more materials selected from the group consisting of sols containing daughter particles and powders of the daughter particles, the daughter particles having an average particle size of not more than 0.2 $\mu$m, and then treating the liquid mixture in a mill and/or an apparatus for high-pressure dispersion, to thereby produce composite fine particles wherein the daughter particles/matrix particles are aggregated in a liquid phase;

(b) coating the composite fine particles produced in step (a) with one or more silicones selected from the group consisting of modified silicones, reactive silicones, and silicone-modified copolymers; and (c) drying and/or pulverizing the composite fine particles coated with the silicone obtained in step (b).

13. An oil dispersion incorporating the ultraviolet shielding composite fine particles as defined in claim 1, obtained by the steps of:

(a) preparing a liquid mixture comprising starting materials for matrix particles which are one or more materials selected from the group consisting of sols containing particles constituting matrix particles and powders of the matrix particles, the matrix particles having a primary particle with an average particle size of from 0.001 to 0.3 μm; and starting materials for daughter particles which are one or more materials selected from the group consisting of sols containing daughter particles and powders of the daughter particles, the daughter particles having an average particle size of not more than 0.2 μm, and treating the liquid mixture in a mill and/or an apparatus for high-pressure dispersion, to thereby produce composite fine particles wherein the daughter particles/matrix particles are aggregated in a liquid phase;

(b) coating the composite fine particles produced in step (a) with one or more silicones selected from the group consisting of modified silicones, reactive silicones, and silicone-modified copolymers; and (c) dispersing in an oil the composite fine particles coated with the silicone obtained in step (b).

14. A method for producing ultraviolet shielding composite fine particles comprising matrix particles and daughter particles, said daughter particles being dispersed in and supported by said matrix particles, the ultraviolet shielding composite fine particles having substantially no catalytic activities and having transparency in a visible light region, the method comprising the steps of:

(a) preparing a liquid mixture comprising starting materials for matrix particles which are one or more materials selected from the group consisting of sols containing particles constituting matrix particles and powders of the matrix particles, the matrix particles having a primary particle with an average particle size of from 0.001 to 0.3 μm; and starting materials for daughter particles which are one or more materials selected from the group consisting of sols containing daughter particles and powders of the daughter particles, the daughter particles having an average particle size of not more than 0.2 μm, and then treating the liquid mixture in a mill and/or an apparatus for high-pressure dispersion, to thereby produce composite fine particles wherein the daughter particles/matrix particles are aggregated in a liquid phase; and (b) coating the composite fine particles produced in step (a) with one or more silicones selected from the group consisting of modified silicones, reactive silicones, and silicone-modified copolymers.

15. The method for producing ultraviolet shielding composite fine particles according to claim 14, comprising matrix particles and daughter particles, said daughter particles being dispersed in and supported by said matrix particles, the ultraviolet shielding composite fine particles having substantially no catalytic activities and having transparency in a visible light region, wherein said method further comprises a step of:

(c) drying and/or pulverizing the composite fine particles coated with the silicone obtained in step (b).

16. The method for incorporating the ultraviolet shielding composite fine particles made by the method of claim 14 in an oil so as to produce an oil dispersion, comprising matrix particles and daughter particles, said daughter particles being dispersed in and supported by said matrix particles, the ultraviolet shielding composite fine particles having substantially no catalytic activities and having transparency in a visible light region, wherein said method further comprises a step of:

(c) dispersing in said oil the composite fine particles coated with the silicone obtained in step (b).

17. Cosmetics comprising the ultraviolet shielding composite fine particles as defined in claim 1.

18. A method of providing ultraviolet protection for human skin by application of the cosmetics according to claim 17, onto human skin.

19. The cosmetics according to claim 17, further containing an ultraviolet protecting agent.

20. The cosmetics according to claim 17, wherein an amount of said ultraviolet shielding composite fine particles is from 0.1 to 30% by weight.

* * * * *